US008187586B2

(12) United States Patent
Brown et al.

(10) Patent No.: US 8,187,586 B2
(45) Date of Patent: May 29, 2012

(54) METHODS OF INDUCING APOPTOSIS IN HYPERPROLIFERATIVE CELLS

(75) Inventors: Arthur M. Brown, Brecksville, OH (US); Barbara A. Wible, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 522 days.

(21) Appl. No.: 10/784,528

(22) Filed: Feb. 23, 2004

(65) Prior Publication Data
US 2004/0259791 A1    Dec. 23, 2004

Related U.S. Application Data

(63) Continuation of application No. 10/000,778, filed on Oct. 31, 2001, now abandoned.

(51) Int. Cl.
*A01N 63/00* (2006.01)
*A01N 65/00* (2009.01)
*A61K 48/00* (2006.01)
*C12N 15/00* (2006.01)

(52) U.S. Cl. ..................... 424/93.2; 424/93.1; 424/93.6; 435/320.1

(58) Field of Classification Search .................. None
See application file for complete search history.

(56) References Cited

U.S. PATENT DOCUMENTS
6,207,422 B1    3/2001    Brown et al.

OTHER PUBLICATIONS

Bowie, et al. Science, 247: 1306-10, 1990.*
Skolnick et al. Tibtech 18:34-39, 2000.*
Kerbel Cancer & Metastasis Rev. 17:301-304; 1999.*
Vieweg et al. Cancer Investigation, 13(2):193-201; 1995.*
Hoffman Invest. New Drugs 17: 343-360; 1999.*
Wang Eur. J. Physiol. 448:274-286; 2004.*
Shieh et al. Pharmacol. Rev. 52:557-593;2000.*
"Induction of Apoptosis by Protein Inhibitor of Activated Stat1 through c-Jun NH$_2$-terminal Kinase Activation" by Liu, et al., *The Journal of Biological Chemistry*, vol. 276, No. 29, Sep. 28, 2001, pp. 36624-36631.
"Checkpoints of Dueling Dimers Foil Death Wishes" by Oltvai, et al., *Cell*, vol. 79, 189-192, Oct. 21, 1994.
"In vitro drug sensitivity testing in human gliomas" by Kimmel, et al, *J. Neurosurg*, 66:161-171, 1987.
"Recent Results on the Biology of Hodgkin and Reed-Sternberg cells" by Drexler, *Leukemia and Lymphoma*, vol. 9, pp. 1-25, 1993.

Chapter 7, "Monoclonal Antibodies to Osteogenic Sarcoma Antigens" by Embleton, *Monoclonal Antibodies and Cancer*, edited by George L. Wright, Jr., Marcel Dekker, Inc., New York, 1984, pp. 181-207.
Chapter 15, "Karyology of Cells in Culture" by Hsu, *Tissue Culture Methods and Applications*, edited by Paul F. Kruse, Jr. and M. K. Patterson, Jr., Academic Press, New York, San Francisco, London, 1973, pp. 764-767.
"Culture of Animal Cells: A Manual of Basic Technique" by Freshney, Alan R. IIss, Inc., New York, 1983.
"Another Anniversary for the War on Cancer" by Dermer, *Biotechnology*, vol. 12, Mar. 1994, p. 320.
"Acitivites of Heparin-binding (Acidic Fibroblast) Growth Factor-1 from Its Receptor-binding Activities by Site-directed Mutagenesis of a Single Lysine Residue" by Burgess, et al., *The Journal of Cell Biology*, vol. 111, Nov. 1990, 2129-2138.
"Transforming Growth Factor α: Mutation of Aspartic Acid 47 and Leucine 48 Results in Different Biological Activities" by Lazar, et al., *Molecular and Cellular Biology*, vol. 8, No. 3, Mar. 1988, pp. 1247-1252.
"Studies of Aglycosylated Chimeric Mouse Human IgG" by Tao, et al., *The Journal of Immunology*, vol. 143, No. 8, Oct. 15, 1989, pp. 2595-2601.
"Antigen binding and biological activities of engineered mutant chimeric antibodies with human tumor specificities" by Gillies, et al., *Hum. Antibod. Hybridomas*, 1990, vol. 1, No. 1, 47-54.
*Glossary of Genetics and Cytogenetics*, by Reiger, et al, Springer-Verlag, Berlin Heidelberg New York, 1976, pp. 17-18.
The International Search Report dated Jan. 4, 2005.
"Increased K+ Efflux and Apoptosis Induced by the Potassium Channel Modulatory Protein KChAP/PIAS3β in Prostate Cancer Cells" by Wible, et al., *J. Biol. Chem.* vol. 277, Issue 20, 17852-17862, May 17, 2002.

* cited by examiner

*Primary Examiner* — Anne-Marie Falk
(74) *Attorney, Agent, or Firm* — Tarolli, Sundheim, Covell & Tummino LLP

(57) ABSTRACT

Methods of inducing apoptosis in hyperproliferative cells, particularly cancer cells are provided. Such method involves increasing the levels of a potassium channel modulatory protein in the cell. Examples of such proteins are native KChAP protein, a biologically active variant of native KChAP protein, or a biologically active KChAP-related protein (collectively referred to hereinafter as "KChAP protein"). In one embodiment, the cells are contacted with the KChAP protein under conditions permitting uptake of the protein by the cells. In another embodiment, the cells are contacted with (i) a nucleic acid encoding the KChAP protein, and (ii) a promoter active in the cancer cell, wherein the promoter is operably linked to the region encoding the KChAP protein, under conditions permitting the uptake of the nucleic acid by the cancer cell. Methods of detecting cancerous cells in a biological sample selected from the group consisting of a colorectal tissue sample or brain tissue sample are also provided. Such method comprises assaying for the presence of elevated levels of KChAP mRNA or KChAP protein in the sample.

11 Claims, 14 Drawing Sheets

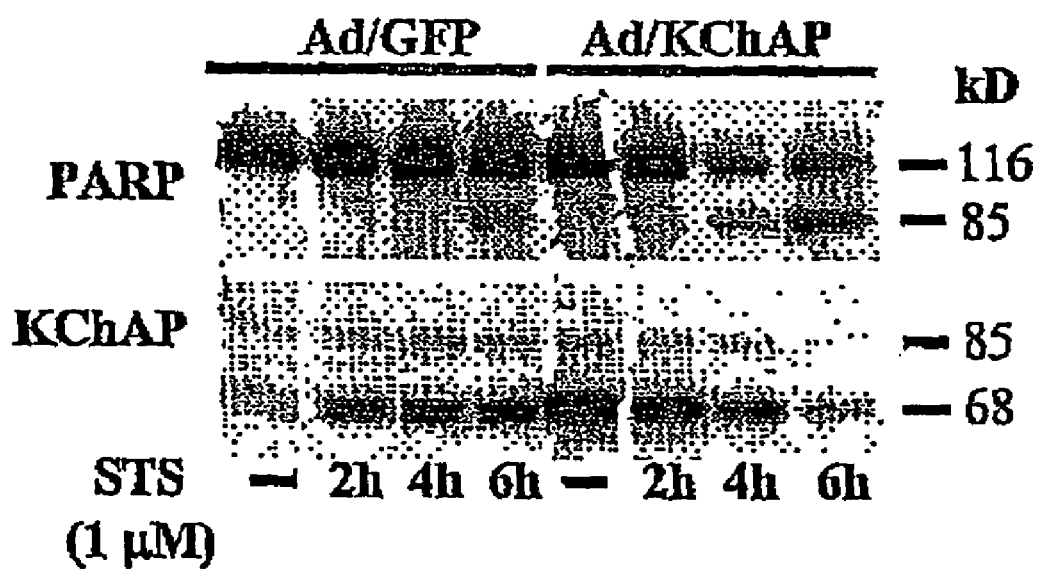
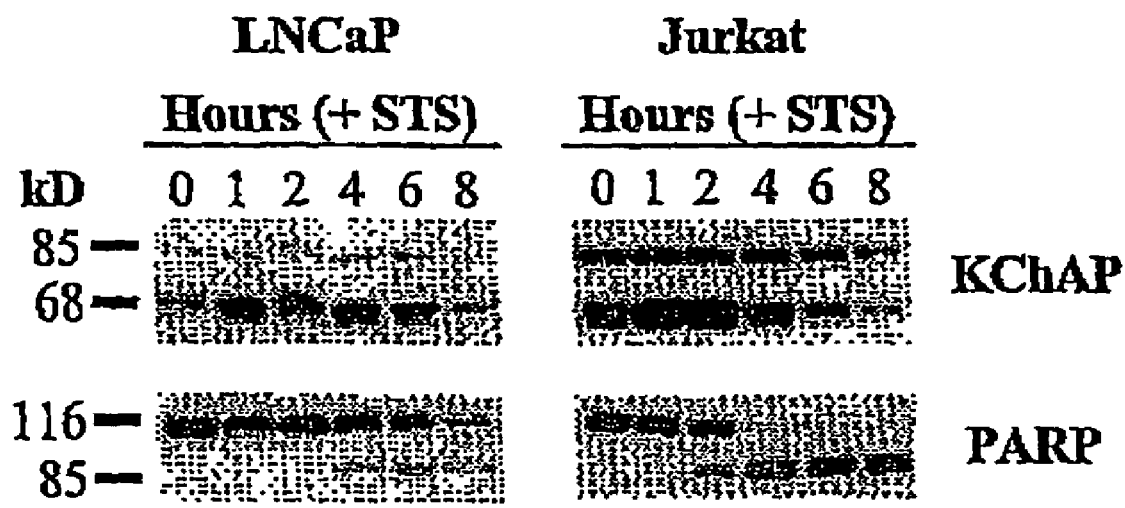
Fig. 2

Fig. 3
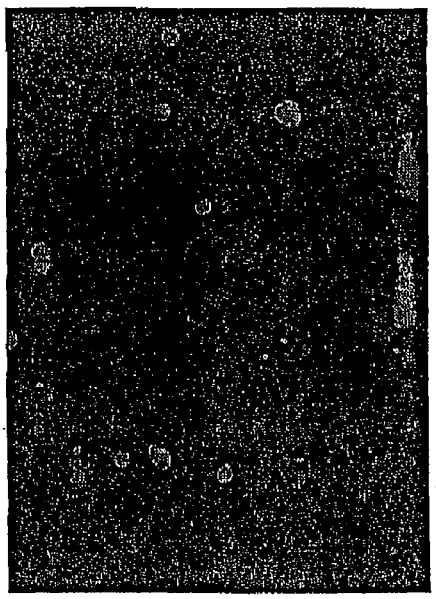
A.
Ad/LacZ
| Infection | % Comet Pos. cells | # cells scored |
|---|---|---|
| 1 | 1.1 | 186 |
| 2 | 1.3 | 234 |
| 3 | 0.9 | 347 |
| 4 | 0 | 279 |
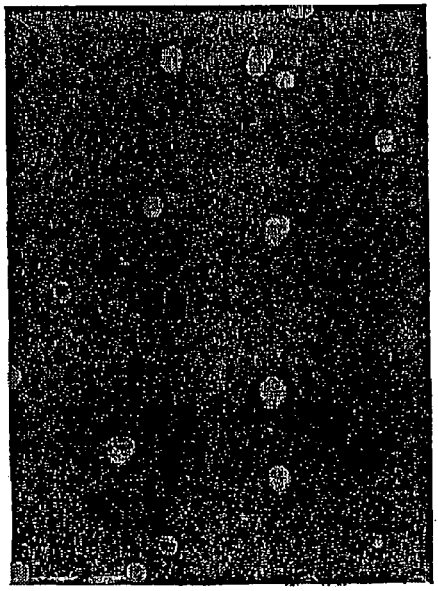
Ad/KChAP
| Infection | % Comet Pos. cells | # cells scored |
|---|---|---|
| 1 | 30.3 | 145 |
| 2 | 27.0 | 148 |
| 3 | 22.4 | 170 |
| 4 | 17.7 | 175 |
B.
Ad/LacZ  Ad/KChAP
KChAP, 088 antibody
PARP Fig. 6
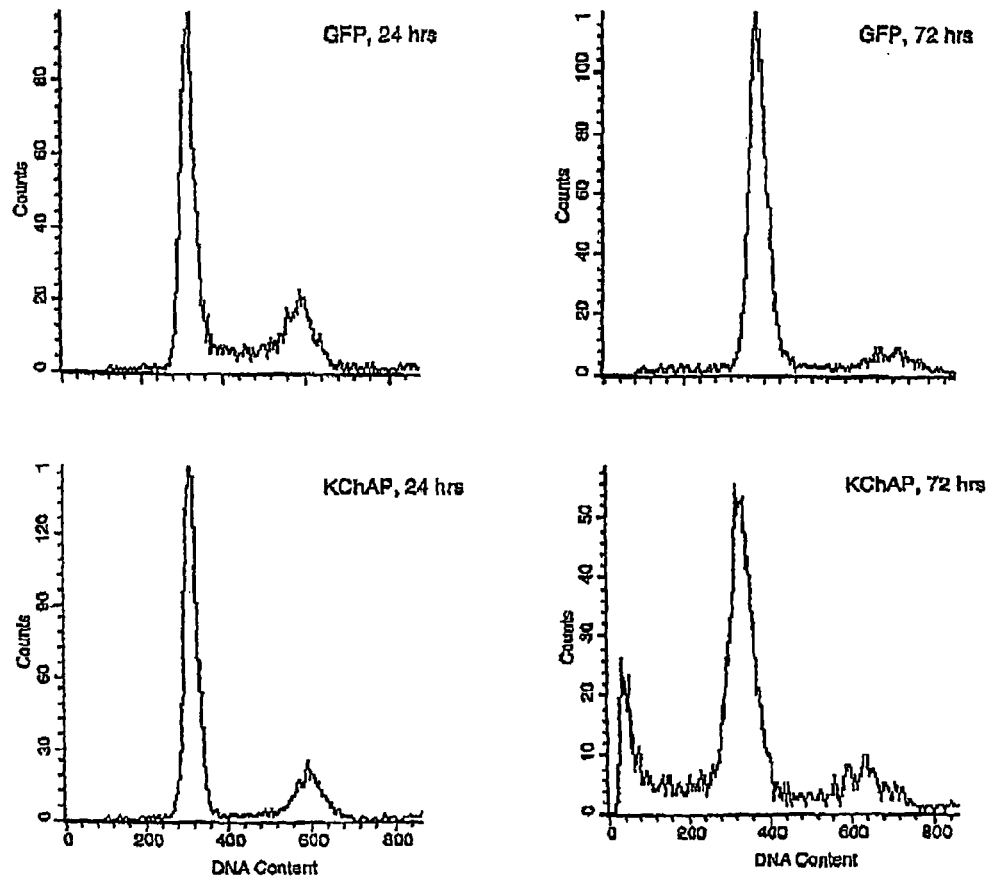
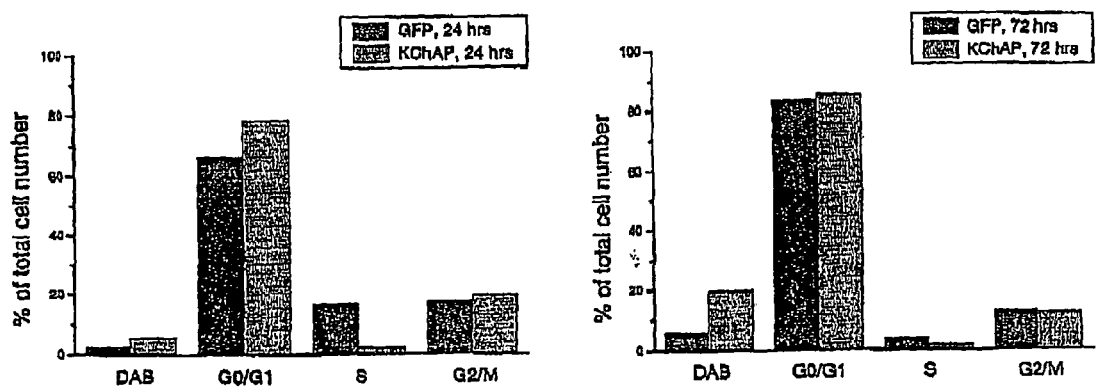

Fig. 8
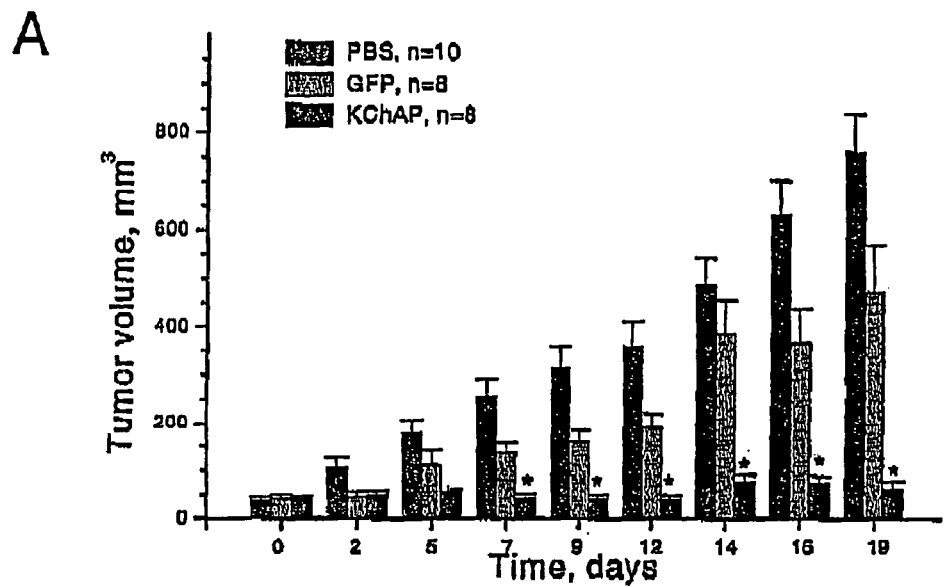
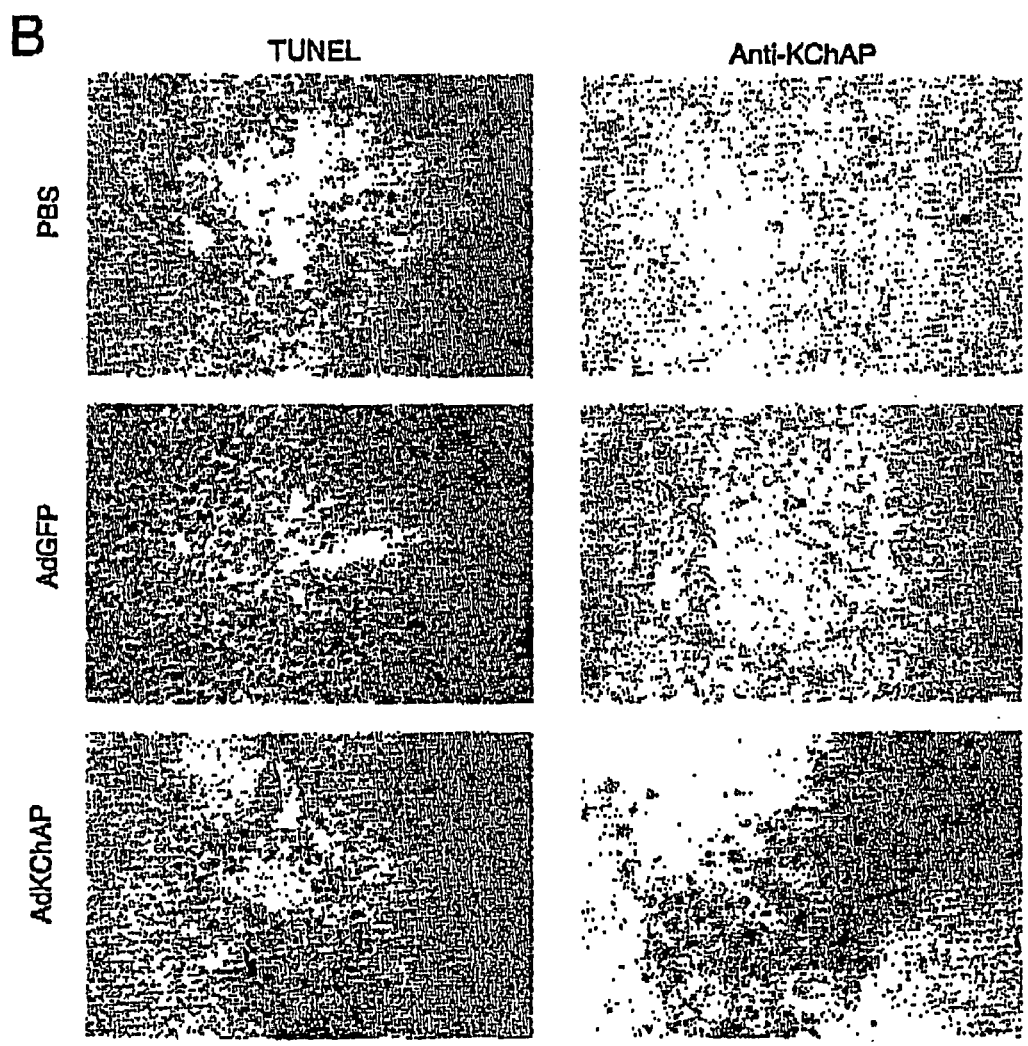

Fig. 9A

```
                                                           A
                                                           p
                                                           a
                                                           I
atgaagatcaaagagctttaccgacgacgctttccccggaagaccctggggccctctgat
---------+---------+---------+---------+---------+---------+
 M  K  I  K  E  L  Y  R  R  R  F  P  R  K  T  L  G  P  S  D   - ctctcccttctctctttgcccctggcacctctcctgtaggctccctggtcctctagct
---------+---------+---------+---------+---------+---------+
 L  S  L  S  L  P  P  G  T  S  P  V  G  S  P  G  P  L  A     -

A
                                          p
                                          a
                                          I
cccattcccccaacgctgttggccctggcaccctgctgggccccaagcgtgaggtggac
---------+---------+---------+---------+---------+---------+
 P  I  P  P  T  L  L  A  P  G  T  L  L  G  P  K  R  E  V  D  - atgcacccccctctgccccagcctgtgcaccctgatgtcaccatgaaaccattgcccttc
---------+---------+---------+---------+---------+---------+
 M  H  P  P  L  P  Q  P  V  H  P  D  V  T  M  K  P  L  P  F  - tatgaagtctatggggagctcatccggcccaccacccttgcatccacttctagccagcgg
---------+---------+---------+---------+---------+---------+
 Y  E  V  Y  G  E  L  I  R  P  T  T  L  A  S  T  S  S  Q  R  - tttgaggaagcgcactttacctttgccctcacacccagcaagtgcagcagattcttaca
---------+---------+---------+---------+---------+---------+
 F  E  E  A  H  F  T  F  A  L  T  P  Q  Q  V  Q  Q  I  L  T  - tccagagaggttctgccaggagccaaatgtgattataccatacaggtgcagctaaggttc
---------+---------+---------+---------+---------+---------+
 S  R  E  V  L  P  G  A  K  C  D  Y  T  I  Q  V  Q  L  R  F  -

P
                           v
                           u
                           I
                           I
tgtctctgtgagaccagctgccccaggaagattattttcccccaacctctttgtcaag
---------+---------+---------+---------+---------+---------+
 C  L  C  E  T  S  C  P  Q  E  D  Y  F  P  P  N  L  F  V  K  -
```

Fig. 9B

```
                         B
                         s
                         t
                         E
                         I
                         I
gttaatgggaaactgtgcccctgccgggttaccttccccaaccaagaatggggccgag
---------+---------+---------+---------+---------+---------+
 V  N  G  K  L  C  P  L  P  G  Y  L  P  P  T  K  N  G  A  E    - cccaagaggcccagccgcccatcaacatcacacccctggctcgactctcagccactgtt
---------+---------+---------+---------+---------+---------+
 P  K  R  P  S  R  P  I  N  I  T  P  L  A  R  L  S  A  T  V    - cccaacaccattgtggtcaattggtcatctgagttcggacggaattactccttgtctgtg
---------+---------+---------+---------+---------+---------+
 P  N  T  I  V  V  N  W  S  S  E  F  G  R  N  Y  S  L  S  V    -

B
              P                                      s
              s                                      a
              t                                      W
              I                                      I
tacctggtgaggcagttgactgcaggaacccttctacaaaaactcagagcaaagggtatc
---------+---------+---------+---------+---------+---------+
 Y  L  V  R  Q  L  T  A  G  T  L  L  Q  K  L  R  A  K  G  I    - cggaacccagaccactcgcgggcactgatcaaggagaaattgactgctgaccctgacagt
---------+---------+---------+---------+---------+---------+
 R  N  P  D  H  S  R  A  L  I  K  E  K  L  T  A  D  P  D  S    - gaggtggccactacaagtctccgggtgtcactcatgtgcccgctagggaagatgcgcctg
---------+---------+---------+---------+---------+---------+
 E  V  A  T  T  S  L  R  V  S  L  M  C  P  L  G  K  M  R  L    -

P
                             s
                             t
                             I
actgtcccttgtcgtgccctcacctgtgcccacctgcagagcttcgatgctgccctttat
---------+---------+---------+---------+---------+---------+
 T  V  P  C  R  A  L  T  C  A  H  L  Q  S  F  D  A  A  L  Y    - ctacagatgaatgagaagaagcctacatggacatgtcctgtgtgtgacaagaaggctccc
---------+---------+---------+---------+---------+---------+
 L  Q  M  N  E  K  K  P  T  W  T  C  P  V  C  D  K  K  A  P    - tatgaatctcttatcattgatggtttatttatggagattcttagttcctgttcagattgt
---------+---------+---------+---------+---------+---------+
 Y  E  S  L  I  I  D  G  L  F  M  E  I  L  S  S  C  S  D  C    -
```

Fig. 9C

```
                  P               B
                  f               a
                  l               m
                  M               H
                  I               I
gatgagatccaattcatggaagatggatcctggtgcccaatgaaacccaagaaggaggca
---------+---------+---------+---------+---------+---------+
   D  E  I  Q  F  M  E  D  G  S  W  C  P  M  K  P  K  K  E  A    -

P
                                  f
                                  l
                                  M
                                  I
tctgaggtttgcccccccgccagggtatgggctggatggcctccagtacagcccagtccag
---------+---------+---------+---------+---------+---------+
   S  E  V  C  P  P  P  G  Y  G  L  D  G  L  Q  Y  S  P  V  Q    - gggggagatccatcagagaataagaagaaggtcgaagttattgacttgacaatagaaagc
---------+---------+---------+---------+---------+---------+
   G  G  D  P  S  E  N  K  K  K  V  E  V  I  D  L  T  I  E  S    -

P
                                                    v
                                                    u
                                                    I
                                                    I
tcatcagatgaggaggatctgccccctaccaagaagcactgttctgtcacctcagctgcc
---------+---------+---------+---------+---------+---------+
   S  S  D  E  E  D  L  P  P  T  K  K  H  C  S  V  T  S  A  A    - atcccggccctacctggaagcaaaggagtcctgacatctggccaccagccatcctcggtg
---------+---------+---------+---------+---------+---------+
   I  P  A  L  P  G  S  K  G  V  L  T  S  G  H  Q  P  S  S  V    - ctaaggagccctgctatgggcacgttgggtggggatttcctgtccagtctcccactacat
---------+---------+---------+---------+---------+---------+
   L  R  S  P  A  M  G  T  L  G  G  D  F  L  S  S  L  P  L  H    - gagtacccacctgccttcccactgggagccgacatccaaggtttagatttattttcattt
---------+---------+---------+---------+---------+---------+
   E  Y  P  P  A  F  P  L  G  A  D  I  Q  G  L  D  L  F  S  F    - cttcagacagagagtcagcactatggcccctctgtcatcacctcactagatgaacaggat
---------+---------+---------+---------+---------+---------+
   L  Q  T  E  S  Q  H  Y  G  P  S  V  I  T  S  L  D  E  Q  D    -
```

Fig. 9D

```
                                                              A
                                                              p
                                                              a
                                                              I
gcccttggccacttcttccagtaccgagggaccccttctcactttctgggcccactggcc
---------+---------+---------+---------+---------+---------+
 A  L  G  H  F  F  Q  Y  R  G  T  P  S  H  F  L  G  P  L  A     -

P              N
                          s              a
                          t              r
                          I              I
cccacgctggggagctcccactgcagcgccactccggcgcccctcctggccgtgtcagc
---------+---------+---------+---------+---------+---------+
 P  T  L  G  S  S  H  C  S  A  T  P  A  P  P  P  G  R  V  S    -

S
                                                     a
                                                     u
                                                     I
agcattgtggcccctggggggggccttgagggagggggcatggaggaccccctgccctcaggt
---------+---------+---------+---------+---------+---------+
 S  I  V  A  P  G  G  A  L  R  E  G  H  G  G  P  L  P  S  G    - ccctctttgactggctgtcggtcagacatcatttccctggactga
---------+---------+---------+---------+-----   1725
 P  S  L  T  G  C  R  S  D  I  I  S  L  D  *    -
```

Enzymes that do cut:

| ApaI | BamHI | BsaWI | BstEII | NarI | PflMI | PstI | PvuII |
|------|-------|-------|--------|------|-------|------|-------|
| SauI |       |       |        |      |       |      |       |

Enzymes that do not cut:

| AatII | AgeI    | AseI  | AvaI  | BbrPI | BfrI  | BglII  | BsaBI |
|-------|---------|-------|-------|-------|-------|--------|-------|
| BsmI  | BssHII  | BstBI | BstXI | ClaI  | DraI  | DraIII | EagI  |
| EcoRI | HindIII | HpaI  | KpnI  | MluI  | NcoI  | NdeI   | NheI  |
| NotI  | NruI    | NsiI  | PmlI  | PvuI  | SacII | SalI   | ScaI  |
| SfiI  | SmaI    | SnaBI | SpeI  | SspI  | StuI  | XbaI   | XhoI  |

Fig. 10

KChAP expression in Human Brain Tumors and Colon Cancers

METHODS OF INDUCING APOPTOSIS IN HYPERPROLIFERATIVE CELLS

CROSS-REFERENCE TO RELATED APPLICATIONS

This application is a continuation of the commonly assigned, U.S. patent application Ser. No. 10/000,778, filed on Oct. 31, 2001 now abandoned.

This invention was made, at least in part, with government support under National Institutes of Health Grant No. HL36930, HL55404, HL61642, HL60759, DK54178. The U.S. government has certain rights in the invention.

FIELD OF THE INVENTION

This invention relates to methods of inducing apoptosis in hyperproliferative cells. More particularly, this invention relates to methods of inducing apoptosis in cancer cells by increasing levels of a potassium channel modulatory protein in such cells.

BACKGROUND

One-third of all individuals in the United States will develop cancer (American Cancer Society Yearly Outlook for 1990). Cancer is second only to cardiac disease as a cause of death in this country (American Cancer Society Yearly Outlook for 1990). Currently, cancer therapy employs a variety of procedures including the administration of chemicals, chemotherapy, radiation, radiotherapy, and surgery.

Radiotherapy is a regional form of treatment used for the control of localized cancers (See Devita, V. T., in Harrison's Principles of Internal Medicine, Braunwald et al., eds., McGraw-Hill Inc., New York, 1987, pp. 431-446). Radiotherapy relies on the fact that some malignant cells are more susceptible to damage by radiation than normal cells. Unfortunately, some tumors cannot be treated with radiotherapy. Moreover, irradiation and radioisotope therapy can induce extensive damage of normal tissues.

Surgery is still considered the primary treatment for most early cancers. Although most tumors are operable, they not fully resectable. Some tumors that appear resectable have micrometastatic disease outside the tumor field. This leads to a recurrence of the cancer close to the initial site of occurrence.

Cancer chemotherapeutic agents, even though widespread in use, have proved to be of limited effect in treating most cancer types. Although there have been some notable successes in the treatment of some specific tumor types (e.g., childhood leukemias) with conventional chemotherapy, more limited success has been obtained in the treatment of solid tumors. This failure is primarily due to the low therapeutic index of many anti-cancer drugs, as well as the intrinsic or acquired drug resistance that often characterizes tumor cells. Another drawback to the use of cytotoxic agents for the treatment of cancer is their severe side effects. These include nausea, vomiting, CNS depression, localized pain, bone marrow depression, bleeding, renal damage, hypo and hyperglycemia, and hypersensitivity reactions. Another drawback is that most anti-cancer drugs are only effective against rapidly dividing cells.

Cancer can be considered as a disturbed balance between the relative rates of cell proliferation and cell death. Until recently, it was thought that the ultimate result of treatment with anti-cancer drugs was cellular necrosis, a form of cell death that involves a swelling of the cells and membrane rupture. Recently, it has been determined that many anti-cancer drugs induce cell death by apoptosis. Apoptotic cell death is an orderly process which is typically accompanied by one or more characteristic morphological and biochemical changes in cells, such as condensation of cytoplasm, loss of plasma membrane microvilli, segmentation of the nucleus, degradation of chromosomal DNA or loss of mitochondrial function. A recognized biochemical marker of apoptosis is the cleavage of chromatin into nucleosomal fragments.

Certain tumor suppressor proteins, such as p53, have been reported to have a role in inducing apoptosis. Apoptosis is also triggered by the activation of a family of cysteine proteases having specificity for aspartic acid residues. These proteases are designated as caspases (Alnemri, et al., Cell, 87:171, (1996)). One identified substrate for caspase-3 is poly (ADP-ribose) polymerase (PARP).

About 50% of human tumors have been shown to have deletions or mutations in the p53 gene and gene product. As a result of this mutation, the cells of these tumors may not be able to undergo apoptosis. This fact may explain the relatively low intrinsic sensitivity of tumors with p53 mutations to conventional chemotherapy.

The need still exists for improved methods for the treatment of most types of cancers. Additional therapeutic methods for inhibiting or reversing the growth of mammalian tumors, particularly human tumors, are desirable. Methods which induce apoptosis of tumor cells or cancer cells, particularly those methods which induce apoptosis of cancer cells in a p53 independent manner, are especially desirable.

SUMMARY OF THE INVENTION

In one aspect, the present invention provides methods of inducing apoptosis in hyperproliferative cells, particularly cancer cells. Such method involves increasing the levels of a potassium channel modulatory protein in the cell. Examples of such proteins arfe native KChAP protein, a biologically active variant of native KChAP protein, or a biologically active KChAP-related protein (collectively referred to hereinafter as "KChAP protein"). In one embodiment, the cells are contacted with the KChAP protein under conditions permitting uptake of the protein by the cells. In another embodiment, the cells are contacted with (i) a nucleic acid encoding the KChAP protein, and (ii) a promoter active in the cancer cell, wherein the promoter is operably linked to the region encoding the KChAP protein, under conditions permitting the uptake of the nucleic acid by the cancer cell. In accordance with the present method, the cancer cells may contain a wild-type or mutant p53 protein. The cancer cells may be in a tissue or cell culture or in a subject. In vivo, the present method can be used to treat a patient with a hyperproliferative disorder, particularly a patient with an epithelial carcinoma, a lymphoma, or leukemia.

In another aspect, the present invention provides a method of inhibiting cell cycling cancer cells that contain a wild-type or native p53 protein. Such method comprises increasing the levels of KChAP protein in such cells.

In another aspect, the present invention provides a method of detecting cancerous cells in a biological sample selected from the group consisting of a colorectal tissue sample or brain tissue sample. In one embodiment, the method comprises contacting the sample or a protein extract therefrom with an antibody to the KChAP protein under conditions wherein antibody binding to one or more epitopes of native KCHAP protein occurs; and assaying for the presence or absence of a complex between the antibody and a protein in the sample, wherein an increase in the level of the antigen-antibody complex, as compared to the levels found in a sample of control cells from the same type of tissue, indicates that the sample comprises cancerous cells. In another embodiment, the method comprises assaying for the presence of KChAP transcript in the sample, wherein a increase in the level of the KChAP transcript in the sample, as compared to the level of the transcript in a control sample, denotes that the test sample comprises cancerous cells.

(A) Overexpression of KChAP in LNCaP cells for 24 hours results in increased basal $Rb^+$ efflux compared to control cells overexpressing GFP. Number of 35-mm wells of cells examined is indicated above bars. * indicates significant difference compared to the control (p<0.005). (B) Flow cytometry of LNCaP cells 72 hours after Ad/KChAP infection. In unfixed cells, intracellular $K^+$ was measured with the $K^+$ binding dye, PBFI and plotted versus propodium iodide (PI) fluorescence (to distinguish between live and dead cells). Cells in R1 (high PI fluorescence) are classified as dead cells. Most uninfected control cells fall into R3 (low PI, normal $K^+$), while Ad/KChAP infected cells show a major shift of the population to R2 (low PI, decreased $K^+$). (C) Comparison of intracellular $K^+$ to cell size in control and Ad/KChAP infected cells. Dead cells in R1 were removed from analysis and those in R2 and R3 were replotted to evaluate $K^+$ as a function of cell size. Cell size was estimated by forward scatter. Decreased intracellular $K^+$ in—overexpressing cells correlated with cell shrinkage. A grid was placed over each panel to emphasize the decreased intracellular $K^+$ seen in—infected cells compared to uninfected cells of the same size.

FIG. 2(A) shows the effect of KChAP overexpression on apoptosis in prostate cancer cells. Apoptosis in LNCaP cells infected with either Ad/GFP or Ad/KChAP (m.o.i. of 100; greater than 95% cells infected) was monitored by examining PARP cleavage on Western blots. KChAP, both endogenous and overexpressed, was detected with the antibody (899).

FIG. 2(B) shows the effect of staurosporine treatment on KChAP and PARP expression in prostate cancer cells. KChAP (68 kD) immunoreactivity increases in LNCaP and Jurkat T-cells treated with staurosporine (STS, 1 µM). Western blot analysis of and PARP expression in lysates of LNCaP and Jurkat cells shows increased reactivity of the 68 kD band with the antibody after treatment with STS. Increased immunoreactivity is maintained until significant PARP cleavage is detected after which the signal drops to below control levels.

FIG. 3 shows the effect of KChAP overexpression on DNA degradation and PARP cleavage in prostate cancer cells.

(A) Comet assay to detect DNA degradation in LNCaP cells three days post-infection with Ad/LacZ or Ad/KChAP (moi=100). Cells were counted from four separate infections. An example of a field of cells examined for each type of infection is shown in the upper panels. Quantitation of each infection is presented below. An average of 0.8% of Ad/LacZ infected cells were Comet positive compared to an average of 24.4% of Ad/KChAP infected cells (p<0.001). (B) Western blot of overexpressed KChAP (detected with 088 antibody) and PARP cleavage in LNCaP lysates prepared from cells as described in (A). Each lane represents lysate from a separate batch of infected cells.

Figure 4:
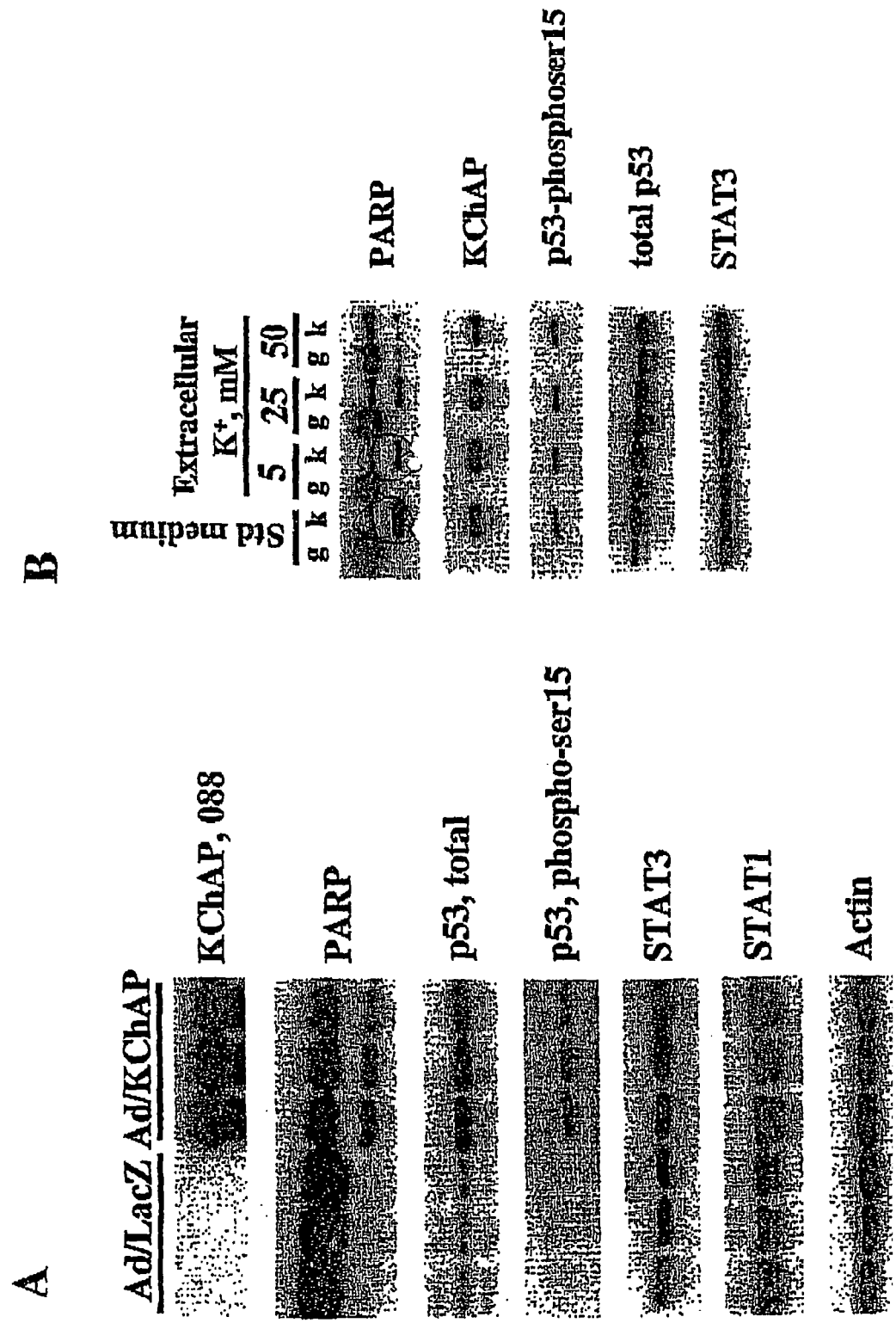

FIG. 4 shows the effect of KChAP overexpression on p53 levels and p53-serine 15 phosphorylation in prostate cancer cells.

(A) Western blot analysis of LNCaP cell lysates prepared three days after infection with Ad/KChAP or Ad/LacZ viruses (moi of 100). Results are shown from triplicate infections. The 088 antibody reacts only with overexpressed, not endogenous, KChAP. Note that KCHAP overexpression is correlated with an increase in total p53 levels (detected with the DO1 antibody) as well as phosphorylation of p53 serine 15. STAT3 and STAT1 levels are not changed. Actin is included as a loading control. (B) LNCaP cells were infected with Ad/GFP (g) or Ad/KChAP (k) (m.o.i.=100) in the presence of standard medium (RPMI/10% FBS) or media in which extracellular $K^+$ was altered (5, 25 or 50 mM) (see methods for details of media preparation). Lysates were prepared 72 hours post-infection and examined by Western blotting for PARP, overexpressed KChAP (088 antibody), p53-phosphoserine15, total p53 (DO1 antibody), and STAT3. STAT3 serves as the loading control.

Figure 5:
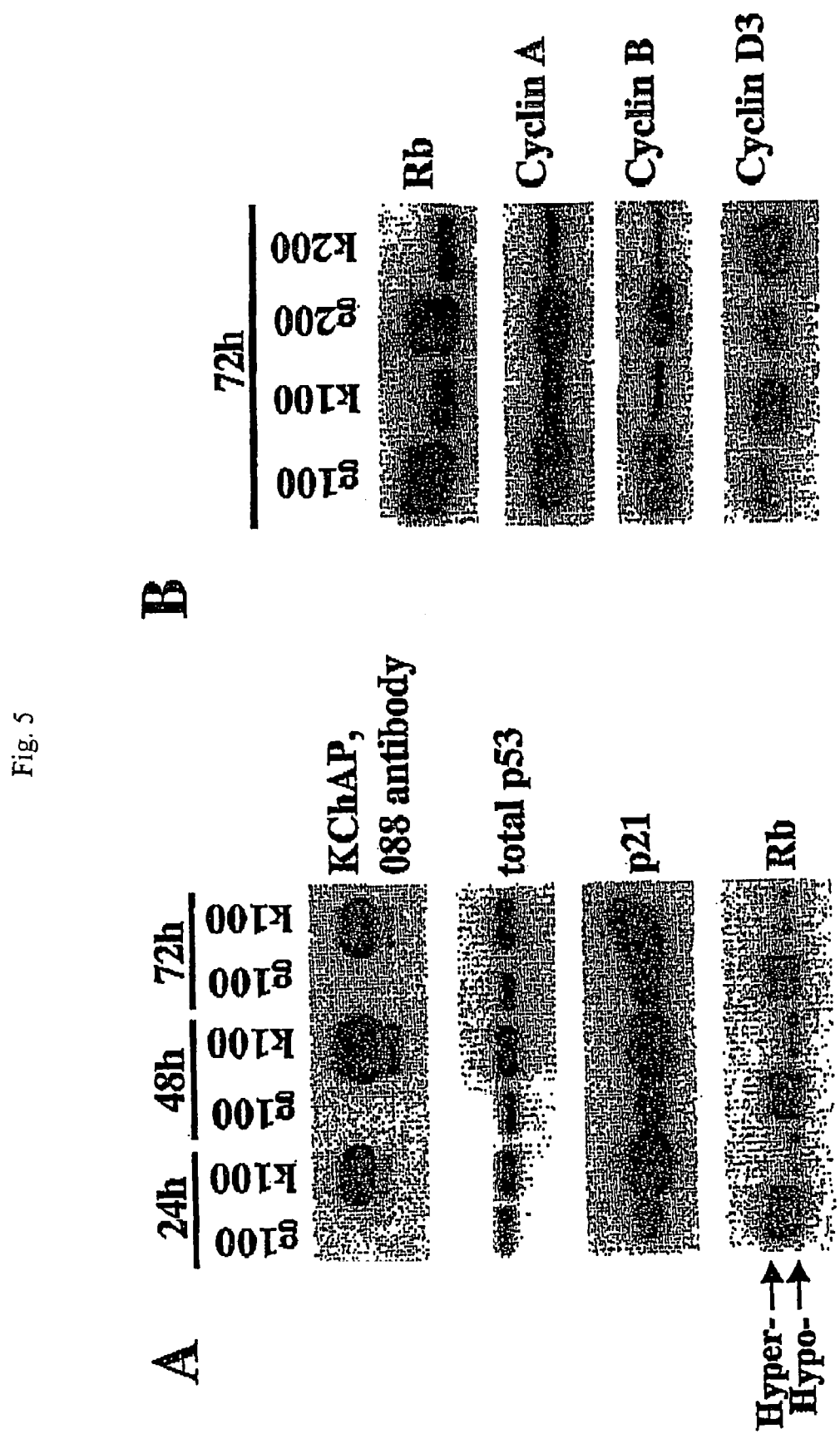

FIG. 5 shows the effect of KChAP overexpression on G0/G1 arrest in prostate cancer cells.

(A) Western blot analysis of LNCaP lysates infected either with Ad/GFP (G) or Ad/KChAP (K) at an moi of 100 (g100 and k100, respectively). Cells were harvested either 24, 48 or 72 hours post-infection. Overexpressed KChAP was detected by the 088 antibody, total p53 by the DO-1 monoclonal. Note that the levels of p21, a transcriptional target of p53 and an inducer of G0/G1 arrest are up in KChAP infected cells as early as 24 hours post-infection. G0/G1 arrest is confirmed by the pattern of Rb (retinoblastoma protein) staining as the hypophosphorylated form predominates at this stage. (B) Western blot analysis of cyclins confirms the G0/G1 arrest mediated by in LNCaP cells. LNCaP cells infected with Ad/GFP or Ad/KChAP at two different moi 100:1 (g100 and k100) and 200:1 (g200 and k200) were examined 72 hours post-infection. Rb expression confirmed G0/G1 arrest as seen in panel A. Consistent with this observation, the levels of two mitotic cyclins A and B were significantly decreased while the level of cyclin D3, a protein predominating in G1, was increased.

FIG. 6 is a flow cytometry analysis of the effects of KChAP overexpression on prostate cancer cells.

(A) LNCaP cells infected with Ad/GFP or Ad/KChAP (both at m.o.i.=100) were fixed in cold 70% ethanol 24 hours (left panel) or 72 hours (right panel) after infection and stained with propidium iodide. Ten thousand cells from each sample were analyzed using FACScan as detailed in Methods. X-axis is propidium iodide intensity, representing DNA content, and the Y-axis is the number of events, representing cell numbers. (B) Histogram of cell cycle distribution. G0/G1, S, and G2-M phases are indicated. The sub-G0/G1 (DAB) population represents apoptotic cells. The data shown are representative of three independent experiments.

Figure 7:
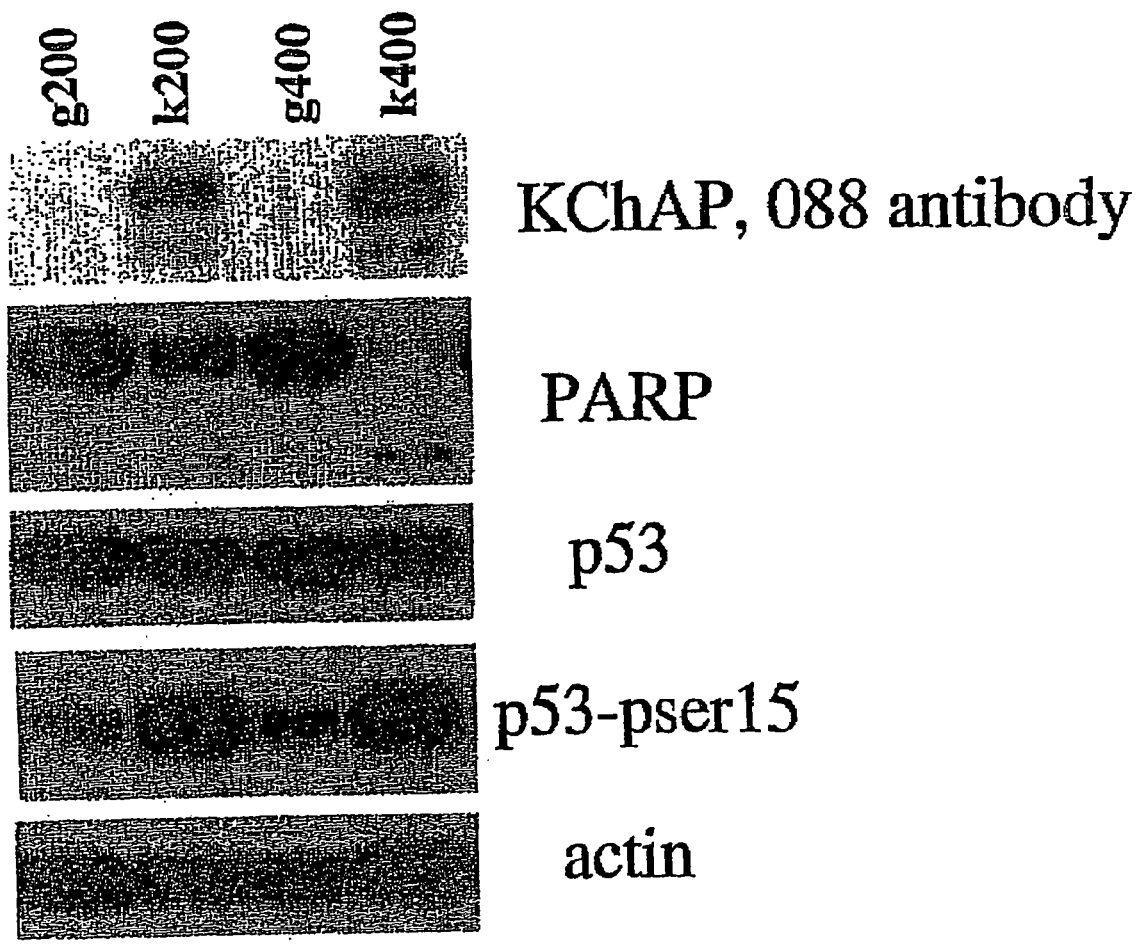

FIG. 7 shows the effect of KChAP overexpression on apoptosis in p53 mutant prostate cancer cells. Western blots of lysates prepared 72 hours post-infection from Du145 cells infected with either Ad/GFP or Ad/KChAP at two different m.o.i., 200 and 400. (g200, g400 and k200, k400, respectively). Overexpressed KChAP was detected with the 088 antibody. The PARP antibody detected both the 116 kD intact protein as well as the 85 kD cleavage product. Steady-state p53 levels were detected with the DO1 monoclonal antibody, and the phosphorylation state of p53-serine 15 was assessed with a specific polyclonal antibody. Actin was included as a loading control.

FIG. 8 shows the effect of Ad/KChAP on growth of Du145 tumor xenographs in nude mice.

(A) Comparison of average Du145 tumor sizes among three treatment groups: PBS, Ad/GFP, Ad/KChAP. Du145 cells injected into the flanks of nude mice were allowed to reach a volume of ~50 mm³ after which the tumors were injected every 48-72 hours with either PBS, Ad/GFP, or Ad/KChAP for a total of 9 injections over a 19-day period. By day 7, the tumor volume of Ad/KChAP injected tumors was significantly less than either PBS or Ad/GFP injected tumors (*p<0.01). There was no significant difference in tumor size between the PBS and Ad/GFP control groups. (B) immunohistochemistry and TUNEL assay in tumor sections from animals sacrificed two days after the last injection (i.e. day 21 after start of treatment). KChAP overexpression was detected in treated tumor sections with the 088 antibody and colorimetric detection (right panels) and corresponding apoptosis was detected with the TUNEL assay (left panels).

FIG. 9 shows the nucleotide sequence (SEQ ID NO. 1) of a cDNA molecule which encodes human KChAP protein and the derived amino sequence (SEQ ID NO. 2) of human KCHAP protein.

Figure 10:
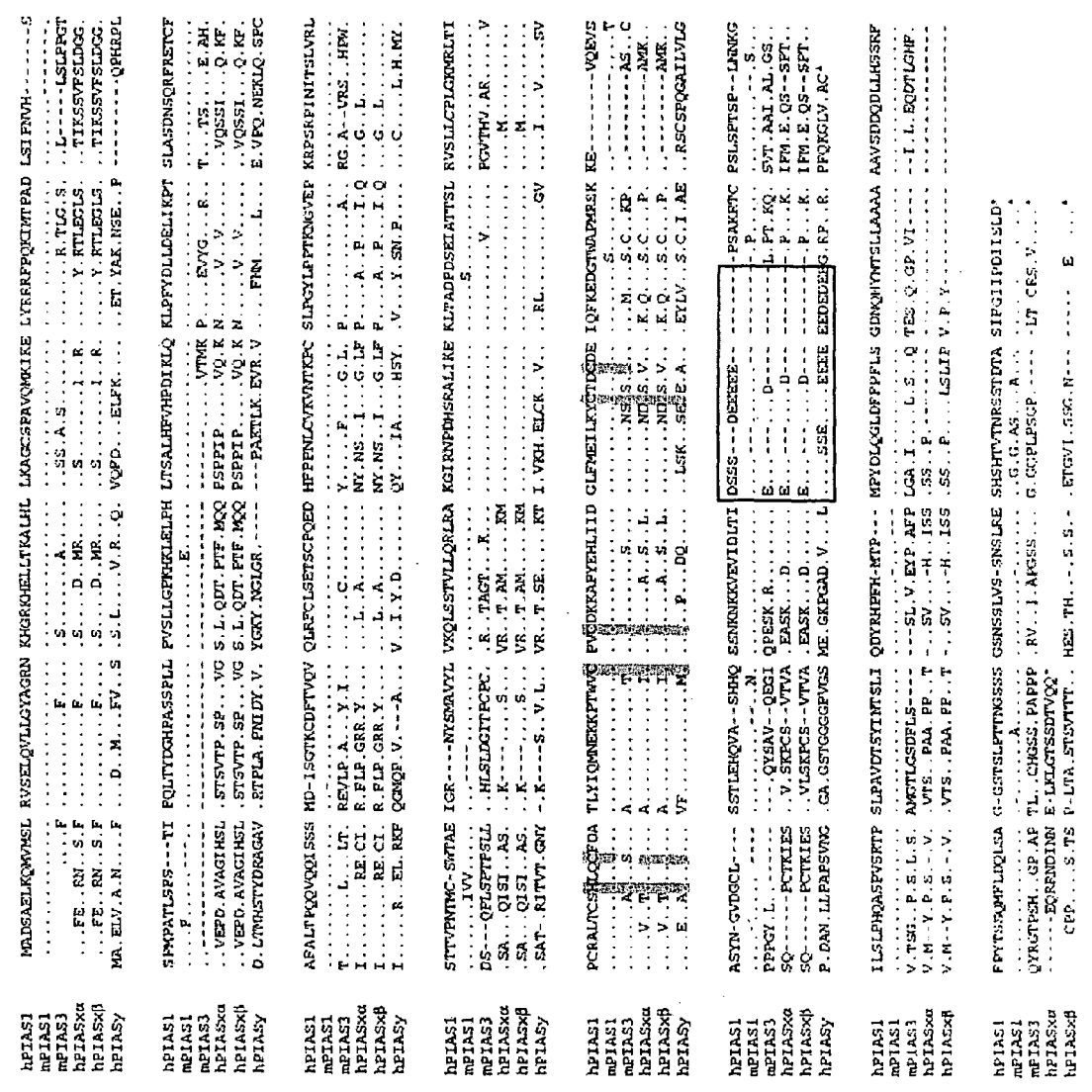

FIG. 10 is a sequence comparison of the PIAS family of proteins (SEQ IS NOS 5-10, respectively, in order of appearance).

Figure 11:
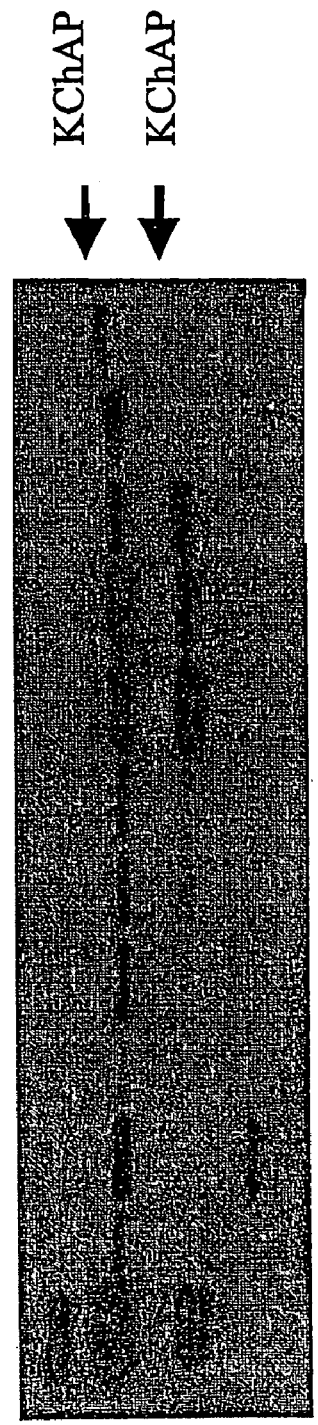

FIG. 11 is a Western blot analysis of KChAP protein levels in cells from a liver cancer cell line (HumI), colorectal cancer tissue (T) and nearby normal tissue (N), and brain tumor tissue (T) 61, 64, 71 and 85) and nearby normal tissue (46, 54, and 86).

DETAILED DESCRIPTION OF THE INVENTION

Definitions

Herein, "apoptosis" is used in a broad sense and refers to the orderly or controlled form of cell death that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured, for instance, by cell viability assays, FACS analysis or DNA electrophoresis, all of which are known in the art. In particular, apoptosis can be measured using the assays described below and in the Examples.

"Antibody" as used herein refers to a protein molecule that binds to, cross reacts with, or is immunoreactive with a specific antigen or immunogen. The binding reaction between an antibody and its antigen is specific in that the antibody binds only to an amino acid sequence present within the specific protein (i.e., an epitope). An anti-KChAP antibody means an antibody molecule that binds to one or more epitopes of native KChAP protein.

"Biological sample" means a sample of mammalian cells. These cells may be part of a tissue or organ sample obtained, for example, by biopsy, or they may be individual cells, for example, cells grown in tissue culture.

"Cancer cell" or "cancerous cell" means a cell in or from a carcinoma, lymphoma, sarcoma or leukemia.

"Prostate cancer" means any of various carcinomas of prostate tissue.

"cDNA" means a DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein.

"Expression" means the production of a protein or a gene transcript (i.e. mRNA) in a cell.

"Hyperproliferative cell" as used herein refers to a cell that exhibits abnormal proliferation. Cancer cells are examples of hyperproliferative cells.

"Label" means to incorporate into a compound a substance that is readily detected. Such substances include radioactive substances and fluorescent dyes, for example.

"Native" means the nucleic acid of a non-mutated gene or peptide sequence encoded by such a gene as found in a phenotypically normal cell.

"Neoplasia" means the process resulting in the formation and growth of an abnormal tissue that grows by cellular proliferation more rapidly than normal, and continues to grow after the stimuli that initiated the new growth ceases.

"Normal cell" means a non-cancerous cell.

"Overexpressing" as used herein means increasing the levels of an intracellular protein to levels above normal.

"Proliferation" means growth and reproduction, i.e., division of cells

"Tumor" refers to a spontaneous, new growth of tissue in the body that forms an abnormal mass. Tumors are comprised of cells and such cells are known as tumor cells. Tumors and cells derived from tumors can be either benign or malignant. Cells that are malignant have a variety of properties that benign cells and non-tumor cells do not have. Malignant cells invade, grow and destroy adjacent tissue, metastasize, and usually grow more rapidly than benign tumor cells. "Neoplasm" is essentially synonymous with tumor.

The terms "treating," "treatment," and "therapy" as used herein refer to curative therapy, prophylactic therapy, and preventative therapy.

The present invention provides a method of inducing apoptosis in a hyperproliferative cell, particularly a cancer cell. The method comprises overexpressing a potassium channel modulatory protein, preferably human KChAP protein or a biologically active equivalent thereof, in the hyperproliferative cell. Such method can be used in vitro or in vivo. Thus, the present method can be serve to treat a patient with a hyperproliferative cell disorder. Hyperproliferative cell disorders include cancers; blood vessel proliferative disorders such as restenosis, atherosclerosis, in-stent stenosis, vascular graft restenosis, etc.; fibrotic disorders; psoriasis; inflammatory disorders, e.g. arthritis, etc.; glomerular nephritis; endometriosis; macular degenerative disorders; benign growth disorders such as prostate enlargement and lipomas; and autoimmune disorders. Cancers are of particular interest, including leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, and benign lesions such as papillomas. The present method is especially useful for treating a patient with an epithelial carcinoma, such as breast cancer or prostate cancer, or a lymphoma, or a leukemia.

The present method is based in part on the discovery that prostate cancer cells comprising wild-type p53 protein and infected with a a non-replicating, recombinant adenovirus containing KChAP cDNA (Ad/KChAP) undergo apoptosis, as assessed by the COMET assay and PARP cleavage, within a period of three days after infection. Ad/KChAP infection increased p53 levels in these prostate cells and increased phosphorylation on p53 residue serine 15, consistent with activation of p53 as a transcription factor. The G1-cell cycle arrest protein p21, was upregulated and infected cells were initially arrested in G1 as assessed by flow cytometry and Western blotting with antibodies to the cell cycle specific proteins, cyclin A, B, and D3, and the retinoblastoma protein Rb.

It has also been determined that p53 is not essential for KChAP-induced apoptosis, as a prostate cancer cell line with mutant p53 also underwent apoptosis when KChAP was overexpressed in such cells. Accordingly, the present method may be used to induce apoptosis in cells which comprise a mutant p53 gene.

In accordance with the present invention, it has also been determined that overexpression of KChAP suppresses growth of prostate tumor xenografts in nude mice. In accordance, with the present invention, it has also been shown that increasing levels of KChAP protein in MCF-7 cells induces apoptosis in these breast cancer cells. It has also been shown that staurosporine a commonly used inducer of apoptosis causes apoptosis in Jurkat cells, which serve as a model for leukemia, and greatly increases their KChAP content. It has also been determined that hyperproliferative cells such as prostate cancer cells and breast cancer cells are about ten times more sensitive to overexpression of KChAP than non-cancerous cells such as cardiomyocytes.

The patent and scientific literature referred to herein establishes the knowledge that is available to those with skill in the art. The issued U.S. patents, allowed applications, and other publications cited herein are hereby incorporated by reference.

KChAP Protein

KChAP protein is a potassium channel modulatory protein that interacts with multiple binding partners ncluding Kvs 1.3, 1.4, 1.5, 2.1, 2.2, 4.2 and 4.3; Kvβ 1.2 and Kvβ 2.1; p53; STAT3; SUMO-1; UBC9; HSF-1 (heat shock factor 1) and BRCA1 and 2. The mature form of KChAP has a calculated molecular weight of about 62.4 kDa. In one embodiment the human KChAP protein has the amino acid sequence shown in FIG. 9 (SEQ ID NO:2). In one embodiment the nucleic acid which encodes the human KChAP protein has the nucleotide sequence shown in FIG. 9, SEQ ID NO. 1. The term KChAP protein encompasses all naturally occurring proteins that comprise a native sequence. Such native sequence KCHAP proteins can be isolated from nature or can be produced by recombinant or synthetic means.

KChAP Related Proteins

KChAP is a member of a protein family referred to as the PIAS family. PIAS is the acronym for Protein Inhibitor of Activated STAT. Other members of the PIAS family include PIAS1, PIASxα, PIASxβ and PIASy, and PIAS3β. PIAS3β is a related-protein whose amino acid sequence is identical to SEQ ID NO. 1, except that it lacks a 39 amino acid insert that is present at the N-terminus of. PIAS3β has been shown to interact with activated STAT3 and potassium channels. FIG. 10 shows the amino acid homology between certain members of this family. With respect to cellular distribution the PIAS proteins are strongly localized to the nucleus where they appear to act as inhibitors of transcription via interactions with STATs and co-repressors or co-activators of transcription in particular with respect to nuclear receptors such as androgen, estrogen and glucocorticoid receptors. PIAS proteins are also present in the cytoplasm where they exert their effects on $K^+$ channels and septins. The present apoptosis-inducing method employs PIAS family members that are biologically active. "Biologically active" for the purposes herein means having the ability to induce apoptosis in at least one type of mammalian cell in vivo or ex vivo. In particular, the biologically active KChAP related protein increases $K^+$ efflux, causes cell shrinkage, and activates caspase 3 to produce PARP cleavage.

Variants of KChAP

The present method also employs biologically active variants of the KChAP protein depicted in FIG. 9. The biologically active KChAP variant increases $K^+$ efflux, causes cell shrinkage, and activates caspase 3 to produce PARP cleavage. In addition, the biologically active KChAP variant has at least about 80% amino acid sequence identity with the protein having the deduced amino acid sequence shown in FIG. 9 (SEQ ID NO:2). Such variants include, for instance, proteins wherein one or more amino acid residues are added or deleted at the N- or C-terminus of the sequence of FIG. 9 (SEQ ID NO:2) or one or more amino acid residues within SEQ ID NO. 2 are substituted. Ordinarily, a KChAP variant will have at least about 80% amino acid sequence identity, more preferably at least about 90% amino acid sequence identity, and even more preferably at least about 95% amino acid sequence identity with the amino acid sequence of FIG. 9 (SEQ ID NO:2). Percent (%) amino acid sequence identity with respect to the sequence herein is defined as the percentage of amino acid residues in a candidate sequence that are identical with the amino acid residues in SEQ ID NO. 2, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as ALIGN™ or Megalign (DNASTAR) software. Those skilled in the art can determine appropriate parameters for measuring alignment, including any algorithms needed to achieve maximal alignment over the full length of the sequences being compared. Because of its high amino acid identity with PIAS3β can be classified as both a related protein and a variant.

Preferably, the deletions and additions are located at the amino terminus, the carboxy terminus, or both, of SEQ ID NO. 2. Amino acid substitutions are generally based on the relative similarity of the amino acid side-chain substituents, for example, their hydrophobicity, hydrophilicity, charge, size, and the like.

It is known in the art that certain amino acids may be substituted by other amino acids having a similar hydropathic index score and a similar hydrophilicity value and still result in a protein with similar biological activity, i.e., still obtain a biological functionally equivalent protein. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

Assays for Apoptosis

Examples of assays for apoptosis are as follows:

Comet (Single-Cell Gel Electrophoresis) Assay to Detect Damaged DNA

The Comet assay, or single-cell gel electrophoresis assay, is used for rapid detection and quantitation of DNA damage from single cells. The Comet assay is based on the alkaline lysis of labile DNA at sites of damage. Cells are immobilized in a thin agarose matrix on slides and gently lysed. When subjected to electrophoresis, the unwound, relaxed DNA migrates out of the cells. After staining with a nucleic acid stain, cells that have accumulated DNA damage appear as bright fluorescent comets, with tails of DNA fragmentation or unwinding. In contrast, cells with normal, undamaged DNA appear as round dots, because their intact DNA does not migrate out of the cell.

TUNEL Assay

When DNA strands are cleaved or nicked by nucleases, a large number of 3'-hydroxyl ends are exposed. In the TUNEL assay (terminal deoxynucleotidyl transferase dUTP nick end labeling), these ends are labeled with UTP using mammalian terminal deoxynucleotidyl transferase (TdT), which covalently adds labeled nucleotides to the 3'-hydroxyl ends of these DNA fragments in a template-independent fashion. The UTP is then detected using specific probes (e.g., you can incorporate BrdUTP and then use a fluorescent anti-BrdU antibody). The assay can be used on cells in situ or the cells can be analyzed by flow cytometry.

Apoptosis Assays Using Annexin V Conjugates

The human anticoagulant annexin V is a 35-36 kilodalton, $Ca^{2+}$-dependent phospholipid-binding protein that has a high affinity for phosphatidylserine (PS). In normal viable cells, PS is located on the cytoplasmic surface of the cell membrane. However, in apoptotic cells, PS is translocated from the inner to the outer leaflet of the plasma membrane, where it is associated with lipid "rafts"—regions of the plasma membrane that are insoluble in detergents, high in cholesterol and sphingolipids, that sequester glycosylphosphatidylinositol (GPI)-linked proteins and tyrosine-phosphorylated proteins and that seem to be involved in signal transduction. Annexin V that is conjugated to various detectable molecules (i.e., fluorescent molcules) are reacted with cells thought to be undergoing apoptosis. If PS is located on the outer surface of the plasma membrane, the annexin V conjugate will bind and be detectable.

Apoptosis Assays Based on Protease Activity

Members of the caspase (CED-3/ICE) family of proteases are crucial mediators of the complex biochemical events associated with apoptosis. In particular, caspase-3 (CPP32/apopain), which has a substrate specificity for the amino acid sequence Asp-Glu-Val-Asp (DEVD) (SEQ ID NO: 4), cleaves a number of different proteins, including poly(ADP-ribose) polymerase (PARP), DNA-dependent protein kinase, protein kinase, and actin. Procaspase-3 is released from the mitochondria into the cytoplasm during apoptosis and activated to caspase-3 by an as-yet-unknown enzyme. Assays for caspase comprise addition of substrates for the enzyme that, for example, increase their fluorescence upon cleavage by caspase 3.

Methods of Inducing Apoptosis of Cancer Cells In Vitro

The KChAP polynucleotides and proteins may also be used to induce apoptosis in cancer cells that comprise a native p53 gene or, alternatively, that comprise a mutated or mutant p53 gene. Such cells are derived, for example, from an epithelial carcinoma, such as a mammary carcinoma, or a prostate carcinoma, a lymphoma, or a leukemia. The method involves increasing the levels of KChAP protein in the cancerous cells.

Inducing Apoptosis with KChAP Polynucleotides and Oligonucleotides

In one embodiment, polynucleotides comprising (i) a coding sequence for KChAP protein, a biologically active variant of KChAP protein, or a biologically active KChAP-related protein, and (ii) a promoter which permits expression of the protein encoded by the coding sequence are introduced into such cells to permit expression or overexpression of the respective protein. Polynucleotides comprising sequences encoding a KChAP protein or a biologically active variant thereof may be synthesized in whole or in part using chemical methods. Polynucleotides which encode a KChAP protein, particularly alleles of the genes which encode a native KChAP protein, may be obtained by screening a genomic library or cDNA library with a probe comprising sequences identical or complementary to the sequences shown in FIG. 9 or with antibodies immunospecific for a protein to identify clones containing such polynucleotide. Variants of the KChAP polynucleotide may be made by site-directed mutagenesis and other methods known in the art.

Viral or plasmid vectors may be used to deliver the KChAP polynucleotide to the cell. "Vector" as used herein refers to a structure composed of covalently linked nucleotides which is able to enter a cell. Alternatively the KChAP polynucleotide may be incorporated into a liposome which, preferably, further comprises a molecule which targets the liposome to the cancer cell.

Viral Vector

Examples of known viral vectors are recombinant viruses which are generally based on several virus classes including poxviruses, herpesviruses, adenoviruses, parvoviruses and retroviruses. Such recombinant viruses generally comprise an exogenous gene under control of a promoter which is able to cause expression of the exogenous gene in vector-infected host cells. Recombinant viruses which can be used to transfect cells are mentioned and cited for example in a review by Mackett, Smith and Moss (1994) J Virol 49(3): 857-864.

Preferably, the virus vector is a defective adenovirus which has the exogenous gene inserted into its genome. The term "defective adenovirus" refers to an adenovirus incapable of autonomously replicating in the target cell. Generally, the genome of the defective adenovirus lacks the sequences necessary for the replication of the virus in the infected cell. Such sequences are partially or, preferably, completely, removed from the genome. To be able to infect target cells, the defective virus must contain sufficient sequences from the original genome to permit encapsulation of the viral particles during in vitro preparation of the construct.

Preferably, the adenovirus is of a serotype which is not pathogenic for man. Such serotypes include type 2 and 5 adenoviruses (Ad 2 or Ad 5). In the case of the Ad 5 adenoviruses, the sequences necessary for the replication are the E1A and E1B regions. Methods for preparing adenovirus vectors are described in U.S. Pat. No. 5,932,210, which issued in August, 1999 to Gregory et al., U.S. Pat. No. 5,985,846 which issued in November, 1999 to Kochanek et al, and U.S. Pat. No. 6,033,908 which issued in March, 2000, to Bout et al.

More preferably, the virus vector is an immunologically inert adenovirus. As used herein the term "immunologically inert" means the viral vector does not encode viral proteins that activate cellular and humoral host immune responses. Methods for preparing immunologically inert adenoviruses are described in Parks et al., *Proc Natl Acad Sci USA* 1996; 93(24) 13565-70; Leiber, A. et al., *J. Virol.* 1996; 70(12) 8944-60; Hardy s., et al, *J. Virol.* 1997, 71(3): 1842-9; and Morsy et al, *Proc. Natl. Acad. Sci. USA* 1998. 95: 7866-71, all of which are specifically incorporated herein by reference. Such methods involve Cre-loxP recombination. In vitro, Cre-loxP recombination is particularly adaptable to preparation of recombinant adenovirus and offers a method for removing unwanted viral nucleotide sequences. Replication deficient recombinant adenovirus lacks the E1 coding sequences necessary for viral replication. This function is provided by 293 cells, a human embryonic kidney cell line transformed by adenovirus type. First generation adenoviruses are generated by co-transfecting 293 cells with a helper virus and a shuttle plasmid containing the foreign gene of interest. This results in the packaging of virus that replicates both the foreign gene and numerous viral proteins. More recently, 293 cells expressing Cre recombinase, and helper virus containing essential viral sequences and with a packaging signal flanked by loxP sites, have been developed (See Parks et al.) In this system, the helper virus supplies all of the necessary signals for replication and packaging in trans, but is not packaged due to excision of essential sequences flanked by loxP. When 293-Cre cells are co-transfected with this helper virus, and a shuttle plasmid (pRP1001) containing the packaging signal, nonsense "filler DNA", and the foreign gene, only an adenovirus containing filler DNA and the foreign gene is packaged (LoxAv). This results in a viral recombinant that retains the ability to infect target cells and synthesize the foreign gene, but does not produce viral proteins.

Methods for Targeting Cancer cells.

Methods for targeting vectors to cancer cells are described in Nakanishi T, Tamai I, Takaki A, Tsuji A. (2000) Cancer cell-targeted drug delivery utilizing oligopeptide transport activity. *Int. J. Cancer.* 88: 274-280, and Poul Mass., Becerril B, Nielsen U B, Morisson P, Marks JD. (2000) Selection of tumor-specific internalizing human antibodies from phage libraries. *J. Mol. Biol.* 301: 1149-1161, both of which are incorporated herein in their entirety. Methods for delivering isolated oligonucleotides and polynucleotides to cells, including the nucleus of cells, are described in Lebedeva I, Benimetskaya L, Stein Calif., Vilenchik M. (2000) Cellular delivery of antisense oligonucleotides. *Eur. J. Pharm. Biopharm.* 50: 101-119. Review., and Fisher K D, Ulbrich K, Subr V, Ward C M, Mautner V, Blakey D, Seymour L W. (2000) A versatile system for receptor-mediated gene delivery permits increased entry of DNA into target cells, enhanced delivery to the nucleus and elevated rates of transgene expression. *Gene. Ther.* 7: 1337-1343.

Liposomes

In another embodiment an expression construct comprising the KChAP polynucleotide may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat (1991) Targeting of liposomes to hepatocytes. *Targeted Diagn. Ther* 4: 87-103). Also contemplated are lipofectamine—DNA complexes.

Inducing Apoptosis in Cancer Cells with KChAP Protein and Biologically Active Equivalents Thereof Apoptosis may be induced in cancer cells, particularly prostate cancer cells, by introducing an KChAP protein, or a biologically active KCHAP variant, or biologically active KChAP related protein into the cancer cell. A variety of methods exist for introducing proteins and polypeptides into cells. Such methods include, but are not limited to, "protein transduction" or "protein therapy" as described in publications by Nagahara et al. (Nagahara, et al., 1998, Nat Med, 4:1449-52.) and in publications from the laboratory of Dowdy (Nagahara, et al., 1998, Nat Med, 4:1449-52.; Schwarze, et al., 1999, Science, 285:1569-72.; Vocero-Akbani, et al., 2000, Methods Enzymol, 322:508-21; Ho, et al., 2001, Cancer Res, 61:474-7.; Vocero-Akbani, et al., 2001, Methods Enzymol, 332:36-49; Snyder and Dowdy, 2001, Curr Opin Mol Ther, 3:147-52.; Becker-Hapak, et al., 2001, Methods, 24:247-56.), publications which are incorporated herein by reference.

In one embodiment an eleven amino acid sequence, the "protein transduction domain" (PTD), from the human immunodeficiency virus TAT protein (Green and Loewenstein, 1988, Cell, 55:1179-88.; Frankel and Pabo, 1988, Cell, 55:1189-93.) is fused to the protein. The purified protein is then put in contact with the surface of the tumor cells and the cells take up the protein which functions to inhibit or suppress growth of that cell. In the case where it is desired to introduce the protein containing the fused PTD into cells comprising a tumor in a human or animal, the protein is administered to the human by a variety of methods. Preferably, the protein is administered by intratumoral or intralesional injection.

KChAP proteins that contain the fused PTD are preferably made by fusing the DNA sequence encoding the KChAP protein with the DNA sequence encoding the PTD. The resulting KCHAP-PTD fusion gene is preferably incorporated into a vector, for example a plasmid or viral vector, that facilitates introduction of the fusion gene into a organism and expression of the gene at high levels in the organism such that large amounts of the fusion protein are made therein. One such organism in which the vector containing the fusion gene can be expressed is a bacterium, preferably *Escherichia coli*. Other organisms are also commonly used by those skilled in the art. After the fusion protein is expressed at a high level in any of these organisms, the fusion protein is purified from the organism using protein purification techniques well known to those skilled in the art.

Methods of Inducing Apoptosis of Cancer Cells In Vivo

In vivo, KChAP protein is overexpressed in cancer cells by administering a pharmaceutical composition comprising a KChAP protein or a polynuceotide encoding a KChAP protein to a subject in need of the same.

In one aspect the method involves administration of the pharmaceutical composition to the patient via local injection. In another aspect, the pharmaceutical composition itself comprises a targeting component which selectively or preferentially targets the pharmaceutical composition to cancer cells. Local injection and targeted delivery, preferably, are used to reduce or avoid introduction of the KChAP protein or KChAP polynucleotide into normal cells.

Those skilled in the art will recognize that delivery via local injection contemplates the use of a syringe, catheter or similar device, which delivers the pharmaceutical composition to the target site, i.e., to an area exhibiting cellular proliferative disease. Delivery may be direct, i.e., intratumoral, or nearly direct, i.e., intralesional, that is, to an area that is sufficiently close to a tumor so that the active agent exhibits the desired pharmacological activity with respect to the tumor itself. Thus, in one aspect, the pharmaceutical composition is preferably delivered intralesionally or intratumorally.

Examples of pharmaceutical compositions which comprise a targeting component include liposomes that comprise not only the KChAP protein or the KChAP polynucleotide but also a targeting molecule, such as for example an antibody that has higher affinity for tumor cells than normal cells. Such liposomes are referred to as immunoliposomes and have the antibody conjugated to the surface the liposome. The liposomes are loaded with the protein or polynucleotide.

Another example of such a composition is a recombinant virus which comprises a gene encoding a ligand that specifically binds to a molecule on the surface of the tumor cell. When this virus is grown, the virus-encoded ligand is displayed on the surface of the virus capsid or envelope so it is exposed to the tumor cell that is to be infected. The recombinant virus also encodes the protein.

Another example of such a composition is an immunoconjugate in which antibodies or parts thereof are conjugated either to the protein or the polynucleotide The antibody is chosen to be specific for the tumor cell to which the therapeutic molecule is to be delivered.

Another approach employs a ligand that binds specifically to the tumor cells. Such ligand is conjugated to a therapeutic DNA molecule to be introduced into the tumor cells.

Pharmaceutical compositions comprising a targeting component may be administered intravenously or, preferably, intratumoraly. The pharmaceutical composition is administered once or repeatedly in a therapeutically effective amount. As used herein, the term "therapeutically effective amount" means the total amount of each active component of the pharmaceutical formulation or method that is sufficient to show a meaningful subject or patient benefit, i.e., a reduction in tumor size, arrest, or inhibition of tumor growth and/or motility or metastasis, and/or an increase in apoptosis, and/or a reduction the symptoms related to the presence of the tumor.

The therapeutically effective amount of the KChAP-encoding nucleic acid or KChAP protein in the pharmaceutical composition used in the method of the present invention will depend upon the nature and severity of the condition being treated, and on the nature of prior treatments which the patient has undergone. Preferably, the amount of nucleic acid encoding the KChAP protein is from about 0.001 ng to about 1 mg per kg body weight. Initially, the attending physician will administer low doses of the composition and observe the patient's response. Larger doses of composition may be administered until the optimal therapeutic effect is obtained for the patient, and at that point the dosage is not increased further. It may be desirable to administer simultaneously or sequentially a therapeutically effective amount of one or more of the therapeutic compositions of the invention to one individual as a single treatment episode. Ultimately, the attending physician will decide the amount of therapeutic composition with which to treat each individual patient.

When a therapeutically effective amount of the pharmaceutical composition used in the method of the invention is administered by injection, the pharmaceutical composition will preferably be in the form of a pyrogen-free, parenterally-acceptable, aqueous solution. The preparation of such parenterally-acceptable solutions, having due regard to pH, isotonicity, stability, and the like, is within the level of ordinary skill in the art of pharmacology. A preferred pharmaceutical composition for injection should contain, in addition to the vector, an isotonic vehicle such as Sodium Chloride Injection, Ringer's Injection, Dextrose Injection, Dextrose and Sodium Chloride Injection, Lactated Ringer's Injection, phosphate buffered saline (PBS), or other vehicle as known in the art. The pharmaceutical composition used in the method of the present invention may also contain stabilizers, preservatives, buffers, antioxidants, or other additives known to those of skill in the art.

The duration of therapy with the pharmaceutical composition used in the method of the present invention will vary, depending on the unique characteristics of the pharmaceutical composition and the particular therapeutic effect to be achieved, the severity of the disease being treated and the condition and potential idiosyncratic response of each individual patient. Ultimately the attending physician will decide on the appropriate duration of therapy with the pharmaceutical composition used in the method of the present invention.

Methods of Detecting Cancer Cells in Colon, Rectal, and Brain Tissue Samples

A. Methods That Employ Anti-KChAP Anti-Antibodies

In accordance with the present invention, it has been determined that colorectal cancer cells and brain cancer cells have higher intracellular levels of KChAP protein than normal cells obtained from the same type of tissue. Accordingly antibodies immunospecific for KChAP protein are useful diagnostic markers for detecting cancerous cells in a colon tissue sample, rectal tissue sample, or brain tissue sample. The diagnostic method comprises the steps of contacting a sample of test cells or a protein extract thereof with immunospecific anti-KChAP antibodies and assaying for the formation of a complex between the antibodies and a protein in the sample. The cells may be fixed or premeablized to permit interaction between the antibody and intracellular proteins. Interactions between antibodies and a protein or peptide in the sample are detected by radiometric, calorimetric, or fluorometric means. Detection of the antigen-antibody complex may be accomplished by addition of a secondary antibody that is coupled to a detectable tag, such as for example, an enzyme, fluorophore, or chromophore. Formation of higher levels of complex in the test cell as compared to the normal cells indicates that the test cell is cancerous.

The sample may be untreated, or subjected to precipitation; fractionation, separation, or purification before combining with the anti-KChAP protein antibody. In those cases where proteins are extracted from the sample, it is preferred that isolated proteins from the sample be attached to a substrate such as a column, plastic dish, matrix, or membrane, preferably nitrocellulose. For isolated protein, the preferred detection method employs an enzyme-linked immunosorbent assay (ELISA) or a Western immunoblot procedure.

Formation of the complex is indicative of the presence of the KChAP protein in the test sample. Thus, the method is used to determine whether there is a decrease or increase in the levels of the KChAP protein in a test sample as compared to levels of the protein in a control sample and, optionally, to quantify the amount of the KChAP protein in the test sample. Deviation between control and test values establishes the parameters for diagnosing the disease. It is contemplated that the levels of KChAP protein in cancerous cells will be at least 50% greater than the level of protein in non-cancerous cells.

B. Methods That Employ KChAP Polynucleotides and Oligonucleotides

Alternatively, KChAP polynucleotides or fragments thereof may be use to detect or define the borders of, colorectal cancers or brain cancers in patients known to have or suspected of having said cancer. The KChAP polynucleotides of the may be used as probes in Northern analysis to identify tissues which have comparatively higher levels of mRNA. In such procedures total RNA or mRNA is obtained from the cells that are known to be or suspected of being cancerous and from non-cancerous cells, e.g. prostate epithelial cells, preferably from the same patient, and then assayed using the KChAP-designed probe. In general, the non-cancerous cells will be obtained from tissues near but outside the border of the expected carcinoma.

In one example, the coding sequence is radioactively labeled with $^{32}P$ or digoxigenin, and then hybridized in solution to RNA that is isolated from test cells, e.g., mammary epithelial cells suspected of being cancerous, and separated by size using gel electrophoresis and blotted to nitrocellulose paper. After hybridization and washing of the nitrocellulose paper, hybridization of the probe to RNA on the nitrocellulose, as revealed by autoradiography, indicates expression of the mRNA. Increased levels of KChAP mRNA expression in the test cells as compared to levels of KChAP mRNA present in normal epithelial cells derived from the same type of tissue indicates that the test cells are cancerous.

In another embodiment of the present invention, KCHAP probes, labeled as described above, are used to hybridize directly to test cells, e.g. prostate epithelial cells or tissues suspected of being cancerous, and to normal cells derived from the same type of tissue, i.e. control cells. The cells or tissues are fixed before hybridization, using procedures well known to those skilled in the art. Hybridization is performed under conditions similar to those described above. Detection of hybridization, by autoradiography for example, indicates the presence of KChAP transcripts within the cells or tissues. An increase level of KChAP transcripts in the test tissues or cells as compared to control cells indicates that the test cells are cancerous.

Similarly, KCHAP-designed primers may be used in RT-PCR to quantify the amount of mRNA in the test tissues and cells. Alternatively, KChAP-designed primers may be used to analyze tissue sections from human patients by an RT in situ-PCR hybridization protocol as described Nuovo et al (1994) in Am J. Pathol., 144, 659-666, which is specifically incorporated herein by reference.

The invention may be better understood by reference to the following examples, which serve to illustrate but not to limit the present invention.

EXAMPLES

Methods

Cell Culture and Adenovirus infection LNCaP, Du145, and Jurkat cells were obtained from the American Type Culture collection. LNCaP cells is a prostate cancer cell line in which the cancer cells contain native p53 protein. Du145 is a prostate cancer cell line in which the cancer cells contain mutated p53 protein. Jurkat cells serve as a model system for leukemia. LNCaP and Jurkat cells were maintained in RPMI medium with 10% FBS, while Du145 cells were propagated in DMEM medium plus 10% FBS. All media also contained 100 units/ml penicillin and 100 μg/ml streptomycin.

A replication-defective, recombinant KCHAP/adenovirus was constructed as follows. Full-length KCHAP cDNA was subcloned in the vector, pShuttle-CMV, and sent to Q-Biogene for adenovirus construction and purification. Expression of from the recombinant adenovirus, Ad/KChAP, was verified by Western blotting lysates of infected cells with a specific antibody, 088, which recognizes only overexpressed (see details below). Recombinant Ad/GFP and Ad/LacZ were purchased from Q-Biogene. Viral infections were performed by diluting the virus to the appropriate concentration in standard medium and overlaying the cells (1 ml/35 mm dish). The media was not changed until the cells were harvested.

Antibodies and Western Blotting Two antibodies were used to monitor intracellular levels of KChAP protein in control and Ad/KChAP infected cells. Antibody 899 was raised against a bacterial fusion protein which consisted of the C-terminal 169 amino acids of KChAP (Wible et al, 1998; Kuryshecv et al 2000). It recognizes both endogenous and overexpressed KChAP. Antibody 088 was raised against a peptide in the N-terminus of KChAP which is not present in PIAS3 (SPSPLASIPPTLLTPGTLL-GPKREVDMH, SEQ ID NO. 3). Antibody 088 recognizes only overexpressed, not endogenous, KChAP. Affinity purified antibodies were used in Western blotting. Other antibodies used for Western blotting to detect the following proteins were obtained from commercial sources: p53 (DO-1; Santa Cruz Biotech.), STAT1, STAT3, and cyclins A, B, and D3 (Transduction Labs), actin (clone AC-40, Sigma), phospho-p53 (ser 15) (Cell Signaling Tech. Inc.), PARP (we used two antibodies interchangeably which recognize both intact and cleaved PARP; one from Cell Signaling Inc., and one from Pharmingen), monoclonal Rb (Pharmingen), and p21 (WAF1 Ab1; Oncogene Res. Pdts).

Cells were lysed in a buffer consisting of 1% Triton-X 100, 150 mM NaCl, 50 mM Tris, 1 mM EDTA, pH 7.5 containing freshly added protease inhibitors (Complete, Roche Mol. Biol.) and the phosphatase inhibitors sodium fluoride (50 mM) and sodium orthovanadate (1 mM) for 30 minutes on ice. Insoluble debris was pelleted at 20,800×g for 10 minutes at 4° C. Lysate protein concentrations were determined by the BCA method (Pierce), and aliquots were boiled in a reducing SDS sample buffer to denature protein. SDS PAGE gels were blotted to PVDF membranes using a semi-dry blotting apparatus. Blots were blocked overnight in 5% milk (Bio-Rad) in PBS-T (PBS plus 0.1% Tween-20) at 4° C. Primary antibodies diluted in blocking buffer were incubated with the blots for one hour at room temperature (RT). Blots were washed with PBS-T and incubated with HRP (horseradish peroxidase)-conjugated secondary antibodies (Amersham Pharmacia) in blocking buffer for 1 hour at RT. Blots were developed with the ECL-Plus kit (Amersham Pharmacia).

COMET Assay DNA degradation was assayed in cells overexpressing Ad/KChAP or Ad/LacZ using the kit from Trevigen.

$Rb^+$ flux LNCaP cells were plated in 6-well tissue culture dishes at 250,000 cells per well. On the following day, cells were infected with either Ad/GFP or Ad/KCHAP (m.o.i.=100). $Rb^+$ fluxes were measured 24 hours after infection using the non-radioactive method of Terstappen (Terstappen, 1999). To load $Rb^+$, cells were incubated for 4 hours (37° C.) in a modified Tyrode's solution containing (in mM): 5 RbCl, 145 NaCl, 1.8 $CaCl_2$, 1 $MgCl_2$, 10 HEPES, 10 glucose (pH 7.4 at 37° C.) and 10% FBS. The cells were then washed 3 times with $Rb^+$ free-PBS and incubated for 10 minutes at room temperature in 1 ml of normal Tyrode's solution. The supernatant containing released $Rb^+$ was collected and the cells were lysed in 1 ml PBS containing 1% Triton X-100 to measure $Rb^+$ remaining in the cells. Samples were diluted (1:4) with ionization buffer (PBS containing 2.5% $HNO_3$) and $Rb^+$ content was determined using flame atomic absorption spectrophotometry at 780 nm (Perkin-Elmer 3100). A calibration curve was constructed to determine $Rb^+$ concentrations. Relative $Rb^+$ efflux was calculated as the amount of $Rb^+$ in the supernatant divided by total $Rb^+$ (supernatant plus cell lysate).

Flow cytometric analysis. Potassium ($K^+$) content At 72 hours post-infection with either Ad/GFP or Ad//KChAP (m.o.i.=100), LNCaP cells were collected by trypsin treatment and washed in PBS. The $K^+$ sensitive dye, potassium-binding benzofuran isophthalate (PBFI), (Molecular Probes) was dissolved in Pluronic F-127 (Molecular Probes), and incubated with the cells in standard medium at a final concentration of 5 μM for 1 hour at 37° C. The cells were then chilled on ice and propidium iodide (5 ug/ml) was added. Flow cytometry was performed with a Becton Dickinson FACS Vantage machine. Ten thousand cells from each treatment group were analyzed. Excitation of PBFI was at 340 nm and emission captured at 425 nm. Propidium iodide was excited by a 488 nm argon laser at the same time.

DNA content For DNA content analysis, cells were trypsinized either 24 or 72 hours post-infection as described above, washed with PBS, and fixed in cold 70% ethanol for at least 8 hours at −20° C. After washing in PBS, propidium iodide (5 μg/ml) was added. Ten thousand cells were examined by flow cytometry for each sample using a Becton Dickinson FACScan (excitation at 488 nm).

Tumor production and adenovirus injection in nude mice Tumor cells (Du145 or LNCaP; $2 \times 10^6$ cells per injection site) were suspended in serum free DMEM, mixed with an equal volume of cold Matrigel on ice, and injected subcutaneously into both flanks of 8-9 week old female Balb/c nude mice. Tumor growth was monitored using calipers every 2 to 3 days. Tumor volume was calculated as $(L \times W^2)/2$, where L is length and W is width in millimeters. When tumors reached an average size of 50-60 mm³ (about 2 weeks for Du145 and 5 weeks for LNCaP), mice were divided into three treatment groups: (1) PBS, (2) Ad/GFP, and (3) Ad/KChAP. Both tumors on an individual mouse received the same treatment. Ad/GFP and Ad/KChAP were diluted in sterile PBS to $5 \times 10^8$ pfu/μl. Injections (1 μl/mm³ of tumor) were delivered directly into the tumors every 2 to 3 days for a total of 3 injections per week. Assuming $10^6$ cells per mm³ of tumor, about 500 pfu of virus per tumor cell was injected at 48-72 hour intervals. Mice were sacrificed by cervical dislocation 48 hours after the final injection, and tumors were dissected and frozen in liquid nitrogen. During the experiments, the animals were housed and handled in accordance with the National Institutes of Health guidelines.

Immunohistochemistry and TUNEL assay of tumor sections Eight-micron sections were prepared from frozen tumors dissected from the three treatment groups (PBS, Ad/GFP, and Ad/KChAP), mounted, and fixed on glass slides. Overexpressed was detected by incubating sections with the 088 antibody (1:100 dilution in 0.2% gelatin/0.5% BSA/PBS) for two hours at room temperature (RT), washing with PBS, and incubating with biotinylated anti-rabbit secondary antibody (1:200) for one hour at RT. Color development was done with the ABC and DAB kits from Vector labs following their instructions. Apoptosis of cells in tumors subjected to different treatments was determined by the terminal deoxynucleotidyl transferase (TdT)-mediated dUTP nick end-labeling (TUNEL) assays using the Apo-Tag kit (Oncor, Inc.), following the manufacturer's instructions.

Example 1

KChAP Overexpression of in Prostate Cancer Cells

KChAP increases $K^+$ Efflux in LNCaP Cells

Figure 1:
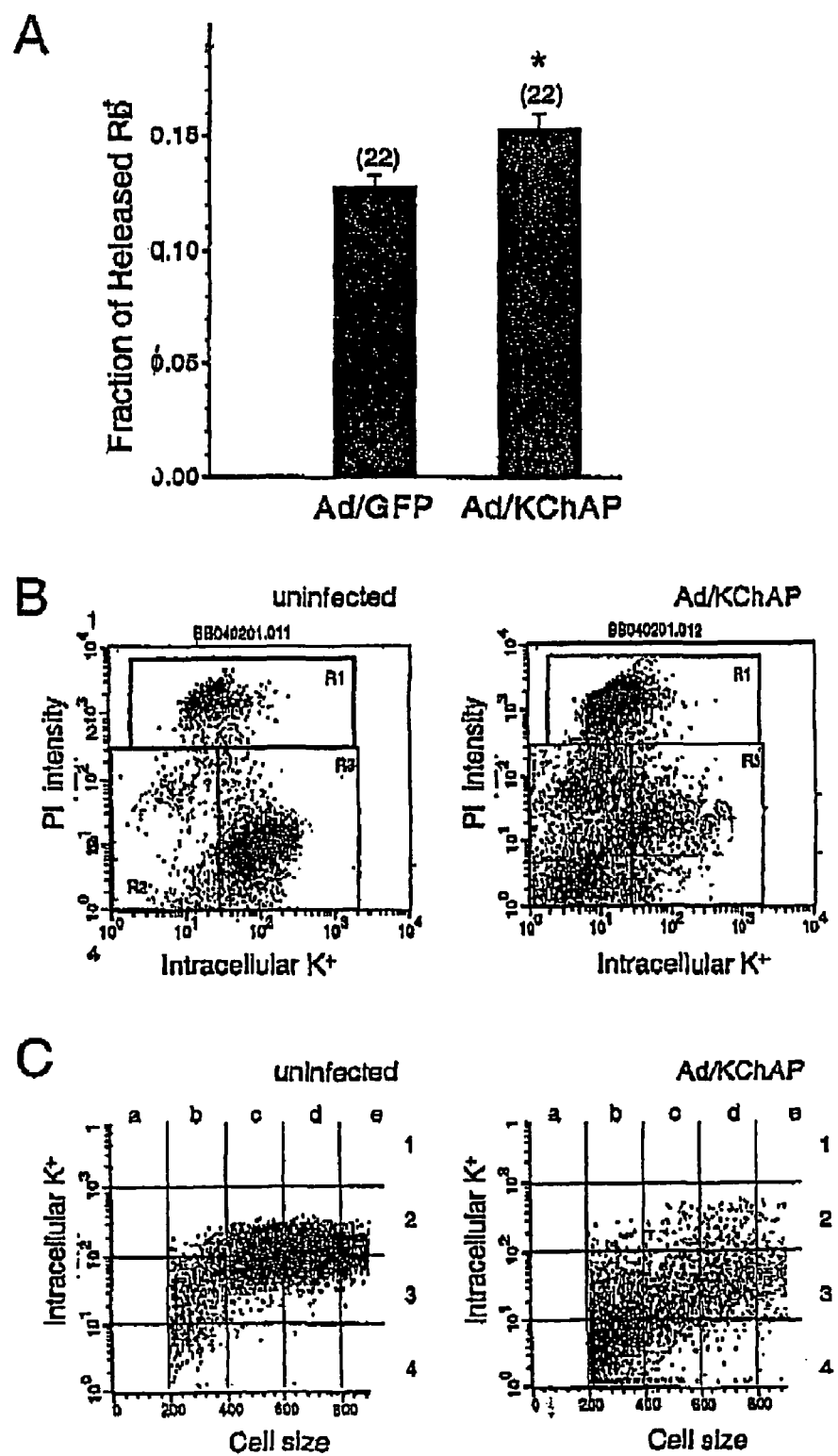
FIG. 1 shows the effect of KChAP overexpression on $K^+$ loss from prostate cancer cells.

To examine the effect of increased intracellular levels of KChAP on $K^+$ flux, LNCaP cells were infected with either Ad/GFP or Ad/KChAP (moi of 100) for 24 hours after which they were loaded with the potassium surrogate rubidium ($Rb^+$) and assayed for $Rb^+$ release by flame atomic absorption spectroscopy. LNCaP are a model cell line for prostate cancer cells which comprise native or wild-type p53 protein. As shown in FIG. 1A, KChAP—overexpressing cells showed a significant increase (about 20%) in the fraction of $Rb^+$ released compared to cells infected with a GFP virus. In a 10 minute period, about 12.5% of the loaded $Rb^+$ was released from Ad/GFP infected cells whereas over 15% was released from cells infected with Ad/KChAP.

The relative amount of $K^+$ in Ad/KChAP-infected cells was measured at later times after infection using flow cytometry with the potassium sensitive dye, PBFI. LNCaP cells were harvested 72 hours post-infection with Ad/KChAP (m.o.i=100). Uninfected cells were used for comparison as the expression of GFP would have interfered with the detection of the dye. In FIG. 1B, the amount of PBFI fluorescence reflecting intracellular $K^+$ was plotted against propidium iodide (PI) fluorescence. Cells with high PI intensity (R1 section) were dead cells and thus not analyzed further. In cells with low PI fluorescence (live cells, sections R2 and R3), there was a clear shift of the population to lower intracellular $K^+$ levels. As we are measuring total $K^+$ and not $K^+$ concentration, this decrease in $K^+$ may reflect cell shrinkage. When the cells in R2 and R3 were replotted to examine cell size (reflected in the forward scatter values collected from the flow cytometer) versus intracellular K+(FIG. 1C), we find that this is the case. In KChAP-infected cells there was a dramatic decrease in average cell size which paralleled the decrease in intracellular $K^+$. Thus, /KChAP stimulated release of $K^+$ from cells when measured 24 hours after introduction of the AD/KChAP virus, and produced a significant decrease in cell size when assessed 72 hours post-infection. From the data in FIG. 1C, it also appeared that the concentration of $K^+$ was decreased in apoptotic, Ad/KChAP infected cells. For example, the smallest uninfected cells fell into the sector b3 (<400 cell size units), while the majority of the smallest-infected cells fell into sector b4.

KChAP Sensitizes Cells to Apoptotic Stimuli

LNCaP cells two days post-infection (moi of 100) with either Ad/GFP or Ad/KChAP were treated with the apoptotic stimulus staurosporine (STS), lysed, and apoptosis assessed by PARP cleavage on Western blots. Staurosporine (STS) was from Sigma and a 1 mM stock solution was prepared in DMSO and stored at −20° C. A final concentration of 1 μM was used to induce apoptosis. As shown in FIG. 2A, no PARP cleavage was detected in cells overexpressing either GFP or KChAP two days after infection. PARP cleavage was detected as early as two hours after the addition of STS (1 μM) in KChAP expressing cells and was about 50% complete at 6 hours. This is in contrast to GFP expressing cells in which PARP cleavage was not detectable at all until 6 hours of STS treatment. KChAP expression was examined with the 899 antibody which detects both endogenous and overexpressed KChAP. Overexpressed KChAP migrates at the same position as the endogenous 68 kD doublet and largely disappears as PARP cleavage progresses. Thus, KChAP makes LNCaP cells more sensitive to STS-induced apoptosis.

We observed an increase in the amount of endogenous KChAP detected in cells exposed to STS. FIG. 2B shows Western blots of endogenous KChAP from both LNCaP and Jurkat cells treated for various lengths of time with 1 μM STS. Multiple bands are detected in both cell lysates with the 899 antibody; a 68 kD doublet which is close to the predicted molecular weight of KChAP and PIAS3 and an upper band of about 85 kD. FIG. 2B shows that the signal of the 68 kD doublet obtained with the 899 antibody is increased as early as one hour after the addition of STS. The signal then drops to control levels or lower after about 6 hours in LNCaP cells and around 4 to 6 hours in Jurkat cells. This peak in immunoreactivity largely precedes detection of PARP cleavage, a marker for apoptosis. Once significant PARP cleavage is detected, much less KChAP is detected by Western blotting. There was no change in the 85 kD band. This phenomenon is not limited to STS as the same pattern was also obtained with the apoptotic inducing drug camptothecin (data not shown). Whether the increased signal on Western blots is due to increased KChAP protein levels or posttranslational modification of the protein to make antibody binding more accessible is not yet known. However, this pattern is consistent with a proapoptotic protein that is upregulated or activated early after the apoptotic stimulus.

KChAP Alone Induces Apoptosis in LNCaP Cells

We saw no PARP cleavage in Ad/KChAP infected LNCaP cells at two days post-infection in the absence of STS. When infected LNCaP cultures were examined microscopically at later times after infection, however, we observed that many of the cells had become detached from the culture dish consistent with cell death. To determine if KChAP overexpression alone is sufficient to induce apoptosis, we assayed for apoptosis in cells three days after infection using the Comet assay to detect DNA degradation. Control infections were done with Ad/LacZ to prevent interference of GFP with the Comet assay.

FIG. 3 shows the results of four independent infections. The top panel shows a typical field of nuclei assayed from cells infected with Ad/LacZ (left) or Ad/KChAP (right). Quantitation of the number of Comet positive cells is presented in the table below. A substantial increase (about 25-fold) in the number of cells with degraded DNA is observed in cells overexpressing KCHAP compared to LacZ (an average of 24.4% comet positive versus 0.8%, respectively).

In addition to the Comet assay, we also examined PARP cleavage in cells three days post-infection (FIG. 3, bottom panel). Lysates from LNCaP cells infected with either Ad/LacZ or Ad/KChAP at an moi of 100 were probed with anti-PARP antibody on Western blots. Lysates from three different batches of infected cells showed detectable PARP cleavage coincident with the expression of KChAP. The antibody 088 which only detects overexpressed KChAP was used to verify AD/KChAP viral infection. Thus, overexpression of KChAP is able to trigger apoptosis in LNCaP cells with both DNA degradation and PARP cleavage apparent three days after infection.

KChAP Overexpression Increases p53 Levels and p53-Serine 15 Phosphorylation p53, a tumor suppressor protein mutated in about 50% of all human cancers, is able to induce apoptosis as well as produce cell cycle (G0/G1) arrest. In yeast two-hybrid experiments, we have found that KChAP is able to interact with p53 (unpublished observations). LNCaP cells have wild-type p53, and low endogenous levels are maintained through a complex set of regulatory mechanisms. Since wild-type p53 can produce apoptosis in many cell types, we examined AD/GFP and Ad/KCHAP infected LNCaP lysates for p53 levels. Western blotting with the DO1 antibody showed an increased amount of total p53 protein in KChAP overexpressing cells three days post-infection (FIG. 4A). The increased p53 levels were coincident with an increase in the reactivity of an antibody specific for p53 phosphorylated on serine 15. We also examined the level of STAT proteins as several members of the PIAS family have been shown to interact with STATs. No changes were detected in either STAT1 or STAT3 levels. These observations suggest that part of the proapoptotic effects of KChAP may be exerted through the upregulation and activation of p53.

To determine if $K^+$ loss is required for KChAP-mediated p53 activation and apoptosis, $K^+$ efflux was blocked by incubating cells in media with high extracellular $K^+$. Cells were infected with Ad/GFP or Ad/KChAP in standard medium or medium with increasing concentrations of $K^+$ (from 5 to 50) and maintained for 72 hours prior to lysis. In these studies, RPMI medium was assembled from the individual components as outlined by Life Technologies Inc. so that we could adjust the $[K^+]$. The total amount of $K^+$ plus $Na^+$ in the media was kept constant at 150 mM so that when $[K^+]$ was elevated, $Na^+$ was correspondingly decreased. FIG. 4B shows that apoptosis, detected by PARP cleavage, is largely blocked in cells bathed in 50 mM $K^+$. There is a small, basal level of PARP cleavage apparent in GFP-expressing cells in 50 mM $K^+$ which is not accentuated in KChAP expressing cells. Even though KChAP-induced apoptosis is blocked in high extracellular $K^+$, phosphorylation of 53 on serine 15 still occurs. Therefore, $K^+$ efflux is not required for p53 activation.

KChAP Produces G0/G1 Cell Cycle Arrest

When p53 is activated as a transcription factor, one of its major targets is the cell cycle arrest protein, p21. Increased p21 expression has been linked to cell cycle arrest at G0/G1. We examined the expression of p21 in Ad/KChAP infected LNCaP cells harvested 24, 48, and 72 hours post-infection.

As shown in FIG. 5A, a dramatic increase in p21 levels was detected by Western blotting as early as 24 hours post-infection. This increased expression was maintained at 48 and 72 hours after infection, and was coincident with elevated p53 levels observed at 24, 48, and 72 hours in KChAP overexpressing cells. Since elevated p21 would be expected to produce G0/G1 arrest, we examined the expression of a cell cycle marker protein, retinoblastoma (Rb). Rb exhibits cell cycle specific phosphorylation (refs): in G0/G1 cells, Rb is hypophosphorylated and migrates more rapidly on SDS PAGE providing a useful marker for cell cycle arrest. In GFP expressing cells, two forms of Rb are detected: an upper, hyperphosphorylated form and a lower, hypophosphorylated form (FIG. 5A). In KChAP expressing cells, only the lower, hypophosphorylated form is detected. This is seen as early as 24 hours post-infection and is maintained throughout the assay period. In FIG. 5B, we examined the expression of several other cyclins as cell cycle markers. Cyclin A and B are mitotic cyclins whose levels decrease during G0/G1 (refs). In—infected LNCaP cells, the levels of both cyclins A and B fall dramatically consistent with G0/G1 arrest. Conversely, a cyclin upregulated during G1 (cyclin D3) is expressed at higher levels in KChAP overexpressing cells. Thus, Western blotting of KChAP-infected cell lysates with cell cycle markers indicates that, in addition to apoptosis, KChAP produces cell cycle arrest at G0/G1.

Cell cycle arrest and apoptosis induced by KChAP were also examined by flow cytometry of infected cells. Ad/GFP and Ad/KCHAP infected cells were fixed either 24 or 72 hours after infection and DNA content assessed by propidium iodide staining. Cells were classified as either DAB (subdiploid), G0/G1 (diploid), S (intermediate), or G2/M (tetraploid). Comparison of the distribution of LNCaP cells after GFP versus KChAP overexpression for 24 hours showed an increase in the population of G0/G1 cells and a decrease in the number of S phase cells among the KChAP infected group (FIG. 6A, left panels). A decrease in the number of S phase cells is consistent with G0/G1 arrest as cells are able to exit S phase but no cells are able to enter from G0/G1. The data are plotted in FIG. 6B (left panel) as the percentage of cells in each population. The percentage of cells in G0/G1 increases from 62% in GFP expressing cells to 78% in KChAP overexpressing cells, while the S phase population drops from 18% in GFP-cells to 1% in KChAP-cells. When assayed 72 hours after infection, there is a dramatic increase in the number of DAB cells in the KChAP expressing group (5% in GFP cells and 20% in KChAP cells; FIGS. 6A and B, right panels). This group of cells with subdiploid DNA content would consist of apoptotic cells with fragmented DNA. Taken together, these data reflect the temporal pattern of the effects of KChAP on LNCaP cells. An early event (within 24 hours after introduction of cDNA) is the arrest of cells in G0/G1. The by induction of apoptosis is detected 72 hours after Ad/KChAP infection.

Example 2

Inducing Apoptosis in Prostate Cancer Cells Comprising a Mutated p53 Protein by Increasing Intracellular Levels of KChAP To determine whether wild-type p53 is essential for KChAP effects, we tested the effects of in a cell line with mutant p53. The prostate cancer cell line, Du145, has p53 with several point mutations rendering it nonfunctional as a transcription factor (ref). Du145 cells were infected with Ad/GFP or Ad/KCHAP at two different m.o.i. (200 and 400)

and lysates prepared 72 hours after infection. Greater than 95% of the cells were infected in these experiments as determined by GFP fluorescence and most of the infected cells were floating by day 3 (data not shown). Western blotting shows significant PARP cleavage in Du145 cells infected with Ad/KChAP compared to control, Ad/GFP infected cells (FIG. 7). Steady-state p53 levels are already high in Du145 cells as is often seen when p53 is mutated, and those levels do not increase with KChAP overexpression. The phosphorylation of p53 on serine 15 is still increased in KChAP overexpressing cells, however. Unlike LNCaP cells, there was no upregulation of p21 evident from Western blots in KChAP-overexpressing Du145 cells (data not shown) suggesting that p53 is not an active transcription factor in Du145 cells. Furthermore, flow cytometry of infected Du145 cells showed that the G0/G1 arrest that was apparent in KChAP-overexpressing LNCaP cells was absent from Du145 cells (data not shown). Taken together, these results suggest that wild-type p53 may be involved in—mediated G0/G1 arrest but is not required for KChAP-induced apoptosis.

Example 3

Inhibiting In Vivo Growth of Subcutaneous Implants of Human Prostate Cancer Cells by Increasing Intracellular Levels of KChAP We have shown that KCHAP is a potent inducer of apoptosis in cell lines with diverse p53 status. To assess its potential usefulness as an anticancer agent, we created subcutaneous tumors in nude mice by injecting either Du145 or LNCaP cells into the flank area. Du145 cells, mixed with matrigel, formed well established tumors in the flanks of nude mice in about two weeks. Once tumors were established, Ad/KChAP was injected directly into the tumors every 48-72 hours for a total of 9 injections over a period of 19 days. Two batches of control tumors were injected with either PBS or Ad/GFP. As shown in FIG. 8A, injection of Ad/KChAP significantly suppressed the growth of Du145 tumors compared with Ad/GFP or PBS treatments. In the animals treated with Ad/KChAP, the mean tumor volume was 81 mm$^3$ after 19 days (n=8). In contrast, the mean tumor volume reached 492 mm$^3$ in the Ad/GFP treated group (n=8) and 716 mm$^3$ in the PBS injected controls (n=10). At the conclusion of the treatment period, mice in the Ad/KChAP treated group were active and appeared normal in contrast to the mice in the other two groups which had difficulty moving because of the tumor burden and appeared ill.

Tumors from each of the three treatment groups were harvested two days after the last injection and processed for immunohistochemistry. When dissected, Ad/KChAP treated tumors were all localized subcutaneously with clear boundaries, while most tumors from the two control groups were found to penetrate into adjacent tissues and organs and had a well established blood supply. Sections were stained with antibody 088 to detect overexpressed KChAP, and parallel sections were assayed for TUNEL positive cells (i.e. apoptotic cells with fragmented DNA). Staining with the 088 antibody was seen in many cells from tumors injected with Ad/KChAP with very little background staining in tumors treated with either Ad/GFP or PBS (FIG. 8B, right panels).

We have seen previously that the 088 antibody does not stain either Du145 or LNCaP cells in culture (unpublished observations). Overexpression of KChAP was accompanied by apoptosis in the infected tumor cells as the comparison of TUNEL positive cells from each of the three treatment groups showed (FIG. 8B, left panels). A low background level of TUNEL positive cells was seen in Ad/GFP and PBS treated tumors with a significant enhancement in the number of TUNEL positive or apoptotic cells seen in—overexpressing tumors.

We also tried LNCaP cells in nude mice, but, in contrast to Du145 cells, LNCaP cells did not generate enough large tumors even 5 weeks after injection of cells to do a complete experiment. However, in a limited number of tumors, we observed similar results with Ad/KChAP injection. Overexpressed KChAP shrunk LNCaP tumors to half their original size while Ad/GFP or PBS treated tumors tripled tumor volume in a 5 week period (data not shown). Immunohistological examination of LNCaP-derived tumor sections showed 088 antibody positive staining which correlated with increased apoptosis and TUNEL positive cells (data not shown). The results indicate that overexpression of KChAP in LNCaP and Du145 prostate cancer cells produces apoptosis and direct injection of Ad/KChAP into xenografts of LNCaP and Du145 tumors in nude mice suppresses tumor growth.

Example 4

Inducing Apoptosis in Breast Cancer Cells by Increasing Intracellular Levels of KChAP Cells from the mammary carcinoma cell line MCF-7 were infected with either Ad/GFP or Ad/KChAP as described above in Example 1. Three days post infection the cells were assayed for PARP cleavage as described above. The results demonstrated the overexpression of KChAP in mammary epithelial cancer cells induces apoptosis.

Example 5

Detection of Cancer Cells with Anti-KChAP Anti-Antibodies

Proteins were extracted from a liver cancer cell line (HumI), colorectal cancer tissue and nearby normal tissue, and brain tumor tissue and nearby normal tissue. Extracted proteins were separated by 6-15% SDS-PAGE, and assayed on a Western blot by reacting with antibody 899. As shown in FIG. 11, the extracts obtained from the liver cell line, the colorectal cancer tissue and brain tumor tissue contained higher levels of than extracts obtained from normal cell lines, normal colorectal tissue, and normal brain tissue respectively. These results demonstrate that intracellular levels of KChAP can be used as a diagnostic marker for liver cancer, colorectal cancer and brain cancer and that a method which employs anti-KChAP antibodies to assess intracellular levels of KChAP can be used to detect liver cancer cells, colorectal cancer cells and brain cancer cells in a tissue sample obtained from a patient.

What is claimed is:

1. A method for inducing apoptosis in human prostate cancer or breast cancer cells comprising:
   delivering to and expressing in said cells a nucleic acid comprising:
   i) a nucleotide sequence encoding human KChAP protein; and
   ii) a promoter active in said cancer cells, wherein the promoter is operably linked to the sequence encoding said protein, wherein said cancer cells are in a tumor in a subject, and wherein said nucleic acid is in a viral vector which is delivered to said cancer cells by intratumoral injection, and further wherein said viral vector is delivered to said cancer cells in an amount effective to cause overexpression of said human KChAP protein as compared to a control level and to induce apoptosis in said cancer cells.

2. The method of claim 1 wherein the cancer cells comprise a native p53 protein.

3. The method of claim 1 wherein the cancer cells comprise a mutant p53 protein.

4. The method of claim 1, wherein the nucleic acid encodes a protein having the sequence set forth in SEQ ID NO: 2.

5. The method of claim 1, wherein said cancer cells are human prostate cancer cells.

6. The method of claim 1, wherein said cancer cells are human breast cancer cells.

7. The method of claim 1, wherein said KChAP protein is expressed in said cancer cells at an amount effective to increase the level of phosphorylation on serine 15 of p53 relative to a control level.

8. The method of claim 1, wherein said KChAP protein is expressed in said cancer cells at an amount effective to decrease the level of cyclins A and B relative to a control level.

9. The method of claim 1, wherein said KChAP protein is expressed in said cancer cells at an amount effective to increase the level of cyclin D3 relative to a control level.

10. The method of claim 1, wherein said KChAP protein is expressed in said cancer cells at an amount effective to increase the level of p53 relative to a control level.

11. The method of claim 1, wherein said KChAP protein is expressed in said cancer cells in an amount effective to increase the level of cleaved poly(ADP-ribose) polymerase (PARP) relative to a control level.

* * * * *

SEQUENCE LISTING

<160> NUMBER OF SEQ ID NOS: 10

<210> SEQ ID NO 1
<211> LENGTH: 1725
<212> TYPE: DNA
<213> ORGANISM: Homo sapiens
<220> FEATURE:
<221> NAME/KEY: CDS
<222> LOCATION: (1)..(1722)

<400> SEQUENCE: 1

| | | | | | | | | | | | | | | | | |
|---|---|---|---|---|---|---|---|---|---|---|---|---|---|---|---|---|
| atg | aag | atc | aaa | gag | ctt | tac | cga | cga | cgc | ttt | ccc | cgg | aag | acc | ctg | 48 |
| Met | Lys | Ile | Lys | Glu | Leu | Tyr | Arg | Arg | Arg | Phe | Pro | Arg | Lys | Thr | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggg | ccc | tct | gat | ctc | tcc | ctt | ctc | tct | ttg | ccc | cct | ggc | acc | tct | cct | 96 |
| Gly | Pro | Ser | Asp | Leu | Ser | Leu | Leu | Ser | Leu | Pro | Pro | Gly | Thr | Ser | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| gta | ggc | tcc | cct | ggt | cct | cta | gct | ccc | att | ccc | cca | acg | ctg | ttg | gcc | 144 |
| Val | Gly | Ser | Pro | Gly | Pro | Leu | Ala | Pro | Ile | Pro | Pro | Thr | Leu | Leu | Ala | |
| | 35 | | | | | 40 | | | | | 45 | | | | | |

| | | | | | | | | | | | | | | | | |
|---|---|---|---|---|---|---|---|---|---|---|---|---|---|---|---|---|
| cct | ggc | acc | ctg | ctg | ggc | ccc | aag | cgt | gag | gtg | gac | atg | cac | ccc | cct | 192 |
| Pro | Gly | Thr | Leu | Leu | Gly | Pro | Lys | Arg | Glu | Val | Asp | Met | His | Pro | Pro | |
| 50 | | | | | 55 | | | | | 60 | | | | | | |

| | | | | | | | | | | | | | | | | |
|---|---|---|---|---|---|---|---|---|---|---|---|---|---|---|---|---|
| ctg | ccc | cag | cct | gtg | cac | cct | gat | gtc | acc | atg | aaa | cca | ttg | ccc | ttc | 240 |
| Leu | Pro | Gln | Pro | Val | His | Pro | Asp | Val | Thr | Met | Lys | Pro | Leu | Pro | Phe | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tat | gaa | gtc | tat | ggg | gag | ctc | atc | cgg | ccc | acc | acc | ctt | gca | tcc | act | 288 |
| Tyr | Glu | Val | Tyr | Gly | Glu | Leu | Ile | Arg | Pro | Thr | Thr | Leu | Ala | Ser | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| tct | agc | cag | cgg | ttt | gag | gaa | gcg | cac | ttt | acc | ttt | gcc | ctc | aca | ccc | 336 |
| Ser | Ser | Gln | Arg | Phe | Glu | Glu | Ala | His | Phe | Thr | Phe | Ala | Leu | Thr | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| cag | caa | gtg | cag | cag | att | ctt | aca | tcc | aga | gag | gtt | ctg | cca | gga | gcc | 384 |
| Gln | Gln | Val | Gln | Gln | Ile | Leu | Thr | Ser | Arg | Glu | Val | Leu | Pro | Gly | Ala | |
| | | | 115 | | | | | 120 | | | | | 125 | | | |

| | | | | | | | | | | | | | | | | |
|---|---|---|---|---|---|---|---|---|---|---|---|---|---|---|---|---|
| aaa | tgt | gat | tat | acc | ata | cag | gtg | cag | cta | agg | ttc | tgt | ctc | tgt | gag | 432 |
| Lys | Cys | Asp | Tyr | Thr | Ile | Gln | Val | Gln | Leu | Arg | Phe | Cys | Leu | Cys | Glu | |
| | 130 | | | | | 135 | | | | | 140 | | | | | |

| | | | | | | | | | | | | | | | | |
|---|---|---|---|---|---|---|---|---|---|---|---|---|---|---|---|---|
| acc | agc | tgc | ccc | cag | gaa | gat | tat | ttt | ccc | ccc | aac | ctc | ttt | gtc | aag | 480 |
| Thr | Ser | Cys | Pro | Gln | Glu | Asp | Tyr | Phe | Pro | Pro | Asn | Leu | Phe | Val | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtt | aat | ggg | aaa | ctg | tgc | ccc | ctg | ccg | ggt | tac | ctt | ccc | cca | acc | aag | 528 |
| Val | Asn | Gly | Lys | Leu | Cys | Pro | Leu | Pro | Gly | Tyr | Leu | Pro | Pro | Thr | Lys | |
| | | | 165 | | | | | 170 | | | | | 175 | | | |

| | | | | | | | | | | | | | | | | |
|---|---|---|---|---|---|---|---|---|---|---|---|---|---|---|---|---|
| aat | ggg | gcc | gag | ccc | aag | agg | ccc | agc | cgc | ccc | atc | aac | atc | aca | ccc | 576 |
| Asn | Gly | Ala | Glu | Pro | Lys | Arg | Pro | Ser | Arg | Pro | Ile | Asn | Ile | Thr | Pro | |
| | | 180 | | | | | 185 | | | | | 190 | | | | |

| | | | | | | | | | | | | | | | | |
|---|---|---|---|---|---|---|---|---|---|---|---|---|---|---|---|---|
| ctg | gct | cga | ctc | tca | gcc | act | gtt | ccc | aac | acc | att | gtg | gtc | aat | tgg | 624 |
| Leu | Ala | Arg | Leu | Ser | Ala | Thr | Val | Pro | Asn | Thr | Ile | Val | Val | Asn | Trp | |
| | | 195 | | | | | 200 | | | | | 205 | | | | |

| | | | | | | | | | | | | | | | | |
|---|---|---|---|---|---|---|---|---|---|---|---|---|---|---|---|---|
| tca | tct | gag | ttc | gga | cgg | aat | tac | tcc | ttg | tct | gtg | tac | ctg | gtg | agg | 672 |
| Ser | Ser | Glu | Phe | Gly | Arg | Asn | Tyr | Ser | Leu | Ser | Val | Tyr | Leu | Val | Arg | |
| | 210 | | | | | 215 | | | | | 220 | | | | | |

| | | | | | | | | | | | | | | | | |
|---|---|---|---|---|---|---|---|---|---|---|---|---|---|---|---|---|
| cag | ttg | act | gca | gga | acc | ctt | cta | caa | aaa | ctc | aga | gca | aag | ggt | atc | 720 |
| Gln | Leu | Thr | Ala | Gly | Thr | Leu | Leu | Gln | Lys | Leu | Arg | Ala | Lys | Gly | Ile | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cgg | aac | cca | gac | cac | tcg | cgg | gca | ctg | atc | aag | gag | aaa | ttg | act | gct | 768 |
| Arg | Asn | Pro | Asp | His | Ser | Arg | Ala | Leu | Ile | Lys | Glu | Lys | Leu | Thr | Ala | |
| | | | | 245 | | | | | 250 | | | | | 255 | | |

| | | | | | | | | | | | | | | | | |
|---|---|---|---|---|---|---|---|---|---|---|---|---|---|---|---|---|
| gac | cct | gac | agt | gag | gtg | gcc | act | aca | agt | ctc | cgg | gtg | tca | ctc | atg | 816 |

```
                                                 -continued

Asp Pro Asp Ser Glu Val Ala Thr Thr Ser Leu Arg Val Ser Leu Met
                     260                 265                 270 tgc ccg cta ggg aag atg cgc ctg act gtc cct tgt cgt gcc ctc acc       864
Cys Pro Leu Gly Lys Met Arg Leu Thr Val Pro Cys Arg Ala Leu Thr
            275                 280                 285 tgt gcc cac ctg cag agc ttc gat gct gcc ctt tat cta cag atg aat       912
Cys Ala His Leu Gln Ser Phe Asp Ala Ala Leu Tyr Leu Gln Met Asn
        290                 295                 300 gag aag aag cct aca tgg aca tgt cct gtg tgt gac aag aag gct ccc       960
Glu Lys Lys Pro Thr Trp Thr Cys Pro Val Cys Asp Lys Lys Ala Pro
305                 310                 315                 320 tat gaa tct ctt atc att gat ggt tta ttt atg gag att ctt agt tcc      1008
Tyr Glu Ser Leu Ile Ile Asp Gly Leu Phe Met Glu Ile Leu Ser Ser
                325                 330                 335 tgt tca gat tgt gat gag atc caa ttc atg gaa gat gga tcc tgg tgc      1056
Cys Ser Asp Cys Asp Glu Ile Gln Phe Met Glu Asp Gly Ser Trp Cys
            340                 345                 350 cca atg aaa ccc aag aag gag gca tct gag gtt tgc ccc cgg cca ggg      1104
Pro Met Lys Pro Lys Lys Glu Ala Ser Glu Val Cys Pro Pro Pro Gly
        355                 360                 365 tat ggg ctg gat ggc ctc cag tac agc cca gtc cag ggg gga gat cca      1152
Tyr Gly Leu Asp Gly Leu Gln Tyr Ser Pro Val Gln Gly Gly Asp Pro
    370                 375                 380 tca gag aat aag aag aag gtc gaa gtt att gac ttg aca ata gaa agc      1200
Ser Glu Asn Lys Lys Lys Val Glu Val Ile Asp Leu Thr Ile Glu Ser
385                 390                 395                 400 tca tca gat gag gag gat ctg ccc cct acc aag aag cac tgt tct gtc      1248
Ser Ser Asp Glu Glu Asp Leu Pro Pro Thr Lys Lys His Cys Ser Val
                405                 410                 415 acc tca gct gcc atc ccg gcc cta cct gga agc aaa gga gtc ctg aca      1296
Thr Ser Ala Ala Ile Pro Ala Leu Pro Gly Ser Lys Gly Val Leu Thr
            420                 425                 430 tct ggc cac cag cca tcc tcg gtg cta agg agc cct gct atg ggc acg      1344
Ser Gly His Gln Pro Ser Ser Val Leu Arg Ser Pro Ala Met Gly Thr
        435                 440                 445 ttg ggt ggg gat ttc ctg tcc agt ctc cca cta cat gag tac cca cct      1392
Leu Gly Gly Asp Phe Leu Ser Ser Leu Pro Leu His Glu Tyr Pro Pro
    450                 455                 460 gcc ttc cca ctg gga gcc gac atc caa ggt tta gat tta ttt tca ttt      1440
Ala Phe Pro Leu Gly Ala Asp Ile Gln Gly Leu Asp Leu Phe Ser Phe
465                 470                 475                 480 ctt cag aca gag agt cag cac tat ggc ccc tct gtc atc acc tca cta      1488
Leu Gln Thr Glu Ser Gln His Tyr Gly Pro Ser Val Ile Thr Ser Leu
                485                 490                 495 gat gaa cag gat gcc ctt ggc cac ttc ttc cag tac cga ggg acc cct      1536
Asp Glu Gln Asp Ala Leu Gly His Phe Phe Gln Tyr Arg Gly Thr Pro
            500                 505                 510 tct cac ttt ctg ggc cca ctg gcc ccc acg ctg ggg agc tcc cac tgc      1584
Ser His Phe Leu Gly Pro Leu Ala Pro Thr Leu Gly Ser Ser His Cys
        515                 520                 525 agc gcc act ccg gcg ccc cct cct ggc cgt gtc agc agc att gtg gcc      1632
Ser Ala Thr Pro Ala Pro Pro Pro Gly Arg Val Ser Ser Ile Val Ala
    530                 535                 540 cct ggg ggg gcc ttg agg gag ggg cat gga gga ccc ctg ccc tca ggt      1680
Pro Gly Gly Ala Leu Arg Glu Gly His Gly Gly Pro Leu Pro Ser Gly
545                 550                 555                 560 ccc tct ttg act ggc tgt cgg tca gac atc att tcc ctg gac tga          1725
Pro Ser Leu Thr Gly Cys Arg Ser Asp Ile Ile Ser Leu Asp
                565                 570
```

```
<210> SEQ ID NO 2
<211> LENGTH: 574
<212> TYPE: PRT
<213> ORGANISM: Homo sapiens

<400> SEQUENCE: 2

Met Lys Ile Lys Glu Leu Tyr Arg Arg Phe Pro Arg Lys Thr Leu
 1               5                  10                  15

Gly Pro Ser Asp Leu Ser Leu Leu Ser Leu Pro Pro Gly Thr Ser Pro
                20                  25                  30

Val Gly Ser Pro Gly Pro Leu Ala Pro Ile Pro Pro Thr Leu Leu Ala
                35                  40                  45

Pro Gly Thr Leu Leu Gly Pro Lys Arg Glu Val Asp Met His Pro Pro
        50                  55                  60

Leu Pro Gln Pro Val His Pro Asp Val Thr Met Lys Pro Leu Pro Phe
 65                  70                  75                  80

Tyr Glu Val Tyr Gly Glu Leu Ile Arg Pro Thr Thr Leu Ala Ser Thr
                    85                  90                  95

Ser Ser Gln Arg Phe Glu Glu Ala His Phe Thr Phe Ala Leu Thr Pro
                100                 105                 110

Gln Gln Val Gln Gln Ile Leu Thr Ser Arg Glu Val Leu Pro Gly Ala
            115                 120                 125

Lys Cys Asp Tyr Thr Ile Gln Val Gln Leu Arg Phe Cys Leu Cys Glu
130                 135                 140

Thr Ser Cys Pro Gln Glu Asp Tyr Phe Pro Pro Asn Leu Phe Val Lys
145                 150                 155                 160

Val Asn Gly Lys Leu Cys Pro Leu Pro Gly Tyr Leu Pro Pro Thr Lys
                    165                 170                 175

Asn Gly Ala Glu Pro Lys Arg Pro Ser Arg Pro Ile Asn Ile Thr Pro
                180                 185                 190

Leu Ala Arg Leu Ser Ala Thr Val Pro Asn Thr Ile Val Val Asn Trp
            195                 200                 205

Ser Ser Glu Phe Gly Arg Asn Tyr Ser Leu Ser Val Tyr Leu Val Arg
            210                 215                 220

Gln Leu Thr Ala Gly Thr Leu Leu Gln Lys Leu Arg Ala Lys Gly Ile
225                 230                 235                 240

Arg Asn Pro Asp His Ser Arg Ala Leu Ile Lys Glu Lys Leu Thr Ala
                    245                 250                 255

Asp Pro Asp Ser Glu Val Ala Thr Thr Ser Leu Arg Val Ser Leu Met
                260                 265                 270

Cys Pro Leu Gly Lys Met Arg Leu Thr Val Pro Cys Arg Ala Leu Thr
            275                 280                 285

Cys Ala His Leu Gln Ser Phe Asp Ala Ala Leu Tyr Leu Gln Met Asn
            290                 295                 300

Glu Lys Lys Pro Thr Trp Thr Cys Pro Val Cys Asp Lys Lys Ala Pro
305                 310                 315                 320

Tyr Glu Ser Leu Ile Ile Asp Gly Leu Phe Met Glu Ile Leu Ser Ser
                    325                 330                 335

Cys Ser Asp Cys Asp Glu Ile Gln Phe Met Glu Asp Gly Ser Trp Cys
                340                 345                 350

Pro Met Lys Pro Lys Lys Glu Ala Ser Glu Val Cys Pro Pro Pro Gly
            355                 360                 365

Tyr Gly Leu Asp Gly Leu Gln Tyr Ser Pro Val Gln Gly Gly Asp Pro
        370                 375                 380

Ser Glu Asn Lys Lys Lys Val Glu Val Ile Asp Leu Thr Ile Glu Ser
```

```
                385                 390                 395                 400
Ser Ser Asp Glu Glu Asp Leu Pro Pro Thr Lys Lys His Cys Ser Val
                405                 410                 415

Thr Ser Ala Ala Ile Pro Ala Leu Pro Gly Ser Lys Gly Val Leu Thr
        420                 425                 430

Ser Gly His Gln Pro Ser Ser Val Leu Arg Ser Pro Ala Met Gly Thr
    435                 440                 445

Leu Gly Gly Asp Phe Leu Ser Ser Leu Pro Leu His Glu Tyr Pro Pro
        450                 455                 460

Ala Phe Pro Leu Gly Ala Asp Ile Gln Gly Leu Asp Leu Phe Ser Phe
465                 470                 475                 480

Leu Gln Thr Glu Ser Gln His Tyr Gly Pro Ser Val Ile Thr Ser Leu
                485                 490                 495

Asp Glu Gln Asp Ala Leu Gly His Phe Phe Gln Tyr Arg Gly Thr Pro
                500                 505                 510

Ser His Phe Leu Gly Pro Leu Ala Pro Thr Leu Gly Ser Ser His Cys
            515                 520                 525

Ser Ala Thr Pro Ala Pro Pro Gly Arg Val Ser Ser Ile Val Ala
    530                 535                 540

Pro Gly Gly Ala Leu Arg Glu Gly His Gly Gly Pro Leu Pro Ser Gly
545                 550                 555                 560

Pro Ser Leu Thr Gly Cys Arg Ser Asp Ile Ile Ser Leu Asp
                565                 570

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Pro Ser Pro Leu Ala Ser Ile Pro Pro Thr Leu Leu Thr Pro Gly
 1               5                  10                  15

Thr Leu Leu Gly Pro Lys Arg Glu Val Asp Met His
            20                  25

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Glu Val Asp
 1

<210> SEQ ID NO 5
<211> LENGTH: 650
<212> TYPE: PRT
<213> ORGANISM: Homo sapiens

<400> SEQUENCE: 5

Met Ala Asp Ser Ala Glu Leu Lys Gln Met Val Met Ser Leu Arg Val
 1               5                  10                  15

Ser Glu Leu Gln Val Leu Leu Gly Tyr Ala Gly Arg Asn Lys His Gly
            20                  25                  30
```

-continued

```
Arg Lys His Glu Leu Leu Thr Lys Ala Leu His Leu Leu Lys Ala Gly
         35                  40                  45

Cys Ser Pro Ala Val Gln Met Lys Ile Lys Glu Leu Tyr Arg Arg Arg
     50                  55                  60

Phe Pro Gln Lys Ile Met Thr Pro Ala Asp Leu Ser Ile Pro Asn Val
 65                  70                  75                  80

His Ser Ser Pro Met Pro Ala Thr Leu Ser Pro Ser Thr Ile Pro Gln
                 85                  90                  95

Leu Thr Tyr Asp Gly His Pro Ala Ser Ser Pro Leu Leu Pro Val Ser
             100                 105                 110

Leu Leu Gly Pro Lys His Lys Leu Glu Leu Pro His Leu Thr Ser Ala
         115                 120                 125

Leu His Pro Val His Pro Asp Ile Lys Leu Gln Lys Leu Pro Phe Tyr
     130                 135                 140

Asp Leu Leu Asp Glu Leu Ile Lys Pro Thr Ser Leu Ala Ser Asp Asn
145                 150                 155                 160

Ser Gln Arg Phe Arg Glu Thr Cys Phe Ala Phe Leu Thr Pro Gln
                 165                 170                 175

Gln Val Gln Gln Ile Ser Ser Ser Met Asp Ile Ser Gly Thr Lys Cys
                 180                 185                 190

Asp Phe Thr Val Gln Val Gln Leu Arg Phe Cys Leu Ser Glu Thr Ser
             195                 200                 205

Cys Pro Gln Glu Asp His Phe Pro Pro Asn Leu Cys Val Lys Val Asn
     210                 215                 220

Thr Lys Pro Cys Ser Leu Pro Gly Tyr Leu Pro Pro Thr Lys Asn Gly
225                 230                 235                 240

Val Glu Pro Lys Arg Pro Ser Arg Pro Ile Asn Ile Thr Ser Leu Val
                 245                 250                 255

Arg Leu Ser Thr Thr Val Pro Asn Thr Met Cys Ser Trp Thr Ala Glu
             260                 265                 270

Ile Gly Arg Asn Tyr Ser Met Ala Val Tyr Leu Val Lys Gln Leu Ser
     275                 280                 285

Ser Thr Val Leu Leu Gln Arg Leu Arg Ala Lys Gly Ile Arg Asn Pro
 290                 295                 300

Asp His Ser Arg Ala Leu Ile Lys Glu Lys Leu Thr Ala Asp Pro Asp
305                 310                 315                 320

Ser Glu Ile Ala Thr Thr Ser Leu Arg Val Ser Leu Leu Cys Pro Leu
                 325                 330                 335

Gly Lys Met Arg Leu Thr Ile Pro Cys Arg Ala Leu Thr Cys Ser His
             340                 345                 350

Leu Gln Cys Phe Asp Ala Thr Leu Tyr Ile Gln Met Asn Glu Lys Lys
     355                 360                 365

Pro Thr Trp Val Cys Pro Val Cys Asp Lys Lys Ala Pro Tyr Glu His
 370                 375                 380

Leu Ile Ile Asp Gly Leu Phe Met Glu Ile Leu Lys Tyr Cys Thr Asp
385                 390                 395                 400

Cys Asp Glu Ile Gln Phe Lys Glu Asp Gly Thr Trp Ala Pro Met Arg
                 405                 410                 415

Ser Lys Lys Glu Val Gln Glu Val Ser Ala Ser Tyr Asn Gly Val Asp
             420                 425                 430

Gly Cys Leu Ser Ser Thr Leu Glu His Gln Val Ala Ser His His Gln
     435                 440                 445

Ser Ser Asn Lys Asn Lys Lys Val Glu Val Ile Asp Leu Thr Ile Asp
 450                 455                 460
```

```
Ser Ser Ser Asp Glu Glu Glu Pro Ser Ala Lys Arg Thr Cys
465                 470                 475                 480

Pro Ser Leu Ser Pro Thr Ser Pro Leu Asn Asn Lys Gly Ile Leu Ser
            485                 490                 495

Leu Pro His Gln Ala Ser Pro Val Ser Arg Thr Pro Ser Leu Pro Ala
            500                 505                 510

Val Asp Thr Ser Tyr Ile Asn Thr Ser Leu Ile Gln Asp Tyr Arg His
            515                 520                 525

Pro Phe His Met Thr Pro Met Pro Tyr Asp Leu Gln Gly Leu Asp Phe
            530                 535                 540

Phe Pro Phe Leu Ser Gly Asp Asn Gln His Tyr Asn Thr Ser Leu Leu
545                 550                 555                 560

Ala Ala Ala Ala Ala Val Ser Asp Asp Gln Asp Leu Leu His Ser
                565                 570                 575

Ser Arg Phe Phe Pro Tyr Thr Ser Ser Gln Met Phe Leu Asp Gln Leu
            580                 585                 590

Ser Ala Gly Gly Ser Thr Ser Leu Pro Thr Thr Asn Gly Ser Ser Ser
            595                 600                 605

Gly Ser Asn Ser Ser Leu Val Ser Ser Asn Ser Leu Arg Glu Ser His
            610                 615                 620

Ser His Thr Val Thr Asn Arg Ser Ser Thr Asp Thr Ala Ser Ile Phe
625                 630                 635                 640

Gly Ile Ile Pro Asp Ile Ile Ser Leu Asp
            645                 650

<210> SEQ ID NO 6
<211> LENGTH: 651
<212> TYPE: PRT
<213> ORGANISM: Mus musculus

<400> SEQUENCE: 6

Met Ala Asp Ser Ala Glu Leu Lys Gln Met Val Met Ser Leu Arg Val
  1               5                  10                  15

Ser Glu Leu Gln Val Leu Leu Gly Tyr Ala Gly Arg Asn Lys His Gly
            20                  25                  30

Arg Lys His Glu Leu Leu Thr Lys Ala Leu His Leu Leu Lys Ala Gly
            35                  40                  45

Cys Ser Pro Ala Val Gln Met Lys Ile Lys Glu Leu Tyr Arg Arg Arg
 50                  55                  60

Phe Pro Gln Lys Ile Met Thr Pro Ala Asp Leu Ser Ile Pro Asn Val
 65                  70                  75                  80

His Ser Ser Pro Met Pro Pro Thr Leu Ser Pro Ser Thr Ile Pro Gln
                85                  90                  95

Leu Thr Tyr Asp Gly His Pro Ala Ser Ser Pro Leu Leu Pro Val Ser
            100                 105                 110

Leu Leu Gly Pro Lys His Glu Leu Glu Leu Pro His Leu Thr Ser Ala
            115                 120                 125

Leu His Pro Val His Pro Asp Ile Lys Leu Gln Lys Leu Pro Phe Tyr
            130                 135                 140

Asp Leu Leu Asp Glu Leu Ile Lys Pro Thr Ser Leu Ala Ser Asp Asn
145                 150                 155                 160

Ser Gln Arg Phe Arg Glu Thr Cys Phe Ala Phe Ala Leu Thr Pro Gln
            165                 170                 175

Gln Val Gln Gln Ile Ser Ser Ser Met Asp Ile Ser Gly Thr Lys Cys
            180                 185                 190
```

```
Asp Phe Thr Val Gln Val Gln Leu Arg Phe Cys Leu Ser Glu Thr Ser
            195                 200                 205

Cys Pro Gln Glu Asp His Phe Pro Pro Asn Leu Cys Val Lys Val Asn
        210                 215                 220

Thr Lys Pro Cys Ser Leu Pro Gly Tyr Leu Pro Thr Lys Asn Gly
225                 230                 235                 240

Val Glu Pro Lys Arg Pro Ser Arg Pro Ile Asn Ile Thr Ser Leu Val
                245                 250                 255

Arg Leu Ser Thr Thr Val Pro Asn Thr Ile Val Val Ser Trp Thr Ala
            260                 265                 270

Glu Ile Gly Arg Asn Tyr Ser Met Ala Val Tyr Leu Val Lys Gln Leu
        275                 280                 285

Ser Ser Thr Val Leu Leu Gln Arg Leu Arg Ala Lys Gly Ile Arg Asn
    290                 295                 300

Pro Asp His Ser Arg Ala Leu Ile Lys Glu Lys Leu Thr Ala Asp Ser
305                 310                 315                 320

Asp Ser Glu Ile Ala Thr Thr Ser Leu Arg Val Ser Leu Leu Cys Pro
                325                 330                 335

Leu Gly Lys Met Arg Leu Thr Ile Pro Cys Arg Ala Leu Thr Cys Ser
            340                 345                 350

His Leu Gln Cys Phe Asp Ala Thr Leu Tyr Ile Gln Met Asn Glu Lys
        355                 360                 365

Lys Pro Thr Trp Val Cys Pro Val Cys Asp Lys Lys Ala Pro Tyr Glu
    370                 375                 380

His Leu Ile Ile Asp Gly Leu Phe Met Glu Ile Leu Lys Tyr Cys Thr
385                 390                 395                 400

Asp Cys Asp Glu Ile Gln Phe Lys Glu Asp Gly Ser Trp Ala Pro Met
                405                 410                 415

Arg Ser Lys Lys Glu Val Gln Glu Val Thr Ala Ser Tyr Asn Gly Val
            420                 425                 430

Asp Gly Cys Leu Ser Ser Thr Leu Glu His Gln Val Ala Ser His Asn
        435                 440                 445

Gln Ser Ser Asn Lys Asn Lys Lys Val Glu Val Ile Asp Leu Thr Ile
    450                 455                 460

Asp Ser Ser Ser Asp Glu Glu Glu Glu Pro Pro Ala Lys Arg Thr
465                 470                 475                 480

Cys Pro Ser Leu Ser Pro Thr Ser Pro Leu Ser Asn Lys Gly Ile Leu
                485                 490                 495

Ser Leu Pro His Gln Ala Ser Pro Val Ser Arg Thr Pro Ser Leu Pro
            500                 505                 510

Ala Val Asp Thr Ser Tyr Ile Asn Thr Ser Leu Ile Gln Asp Tyr Arg
        515                 520                 525

His Pro Phe His Met Thr Pro Met Pro Tyr Asp Leu Gln Gly Leu Asp
    530                 535                 540

Phe Phe Pro Phe Leu Ser Gly Asp Asn Gln His Tyr Asn Thr Ser Leu
545                 550                 555                 560

Leu Ala Ala Ala Ala Ala Val Ser Asp Gln Asp Leu Leu His
                565                 570                 575

Ser Ser Arg Phe Phe Pro Tyr Thr Ser Ser Gln Met Phe Leu Asp Gln
            580                 585                 590

Leu Ser Ala Gly Gly Ser Thr Ser Leu Pro Ala Thr Asn Gly Ser Ser
        595                 600                 605

Ser Gly Ser Asn Ser Ser Leu Val Ser Ser Asn Ser Leu Arg Glu Ser
```

```
                610                 615                 620
His Gly His Gly Val Ala Ser Arg Ser Ser Ala Asp Thr Ala Ser Ile
625                 630                 635                 640

Phe Gly Ile Ile Pro Asp Ile Ile Ser Leu Asp
                645                 650

<210> SEQ ID NO 7
<211> LENGTH: 583
<212> TYPE: PRT
<213> ORGANISM: Mus musculus

<400> SEQUENCE: 7

Met Val Met Ser Phe Arg Val Ser Glu Leu Gln Val Leu Leu Gly Phe
 1               5                  10                  15

Ala Gly Arg Asn Lys Ser Gly Arg Lys His Glu Leu Leu Ala Lys Ala
             20                  25                  30

Leu His Leu Leu Lys Ser Ser Cys Ala Pro Ser Val Gln Met Lys Ile
         35                  40                  45

Lys Glu Leu Tyr Arg Arg Arg Phe Pro Arg Lys Thr Leu Gly Pro Ser
     50                  55                  60

Asp Leu Ser Leu Leu Ser Leu Pro Pro Gly Thr Ser Pro Pro Val His
 65                  70                  75                  80

Pro Asp Val Thr Met Lys Pro Leu Pro Phe Tyr Glu Val Tyr Gly Glu
                 85                  90                  95

Leu Ile Arg Pro Thr Thr Leu Ala Ser Thr Ser Ser Gln Arg Phe Glu
            100                 105                 110

Glu Ala His Phe Thr Phe Ala Leu Thr Pro Gln Gln Leu Gln Gln Ile
        115                 120                 125

Leu Thr Ser Arg Glu Val Leu Pro Gly Ala Lys Cys Asp Tyr Thr Ile
    130                 135                 140

Gln Val Gln Leu Arg Phe Cys Leu Cys Glu Thr Ser Cys Pro Gln Glu
145                 150                 155                 160

Asp Tyr Phe Pro Pro Asn Leu Phe Val Lys Val Asn Gly Lys Leu Cys
                165                 170                 175

Pro Leu Pro Gly Tyr Leu Pro Pro Thr Lys Asn Gly Ala Glu Pro Arg
            180                 185                 190

Gly Pro Ala Val Arg Ser Thr Ser His Pro Trp Leu Asp Ser Gln Pro
        195                 200                 205

Leu Ser Pro Thr Pro Ser Leu Leu Ile Gly His Leu Ser Leu Asp Gly
    210                 215                 220

Ile Thr Pro Cys Pro Cys Leu Val Arg Gln Leu Thr Ala Gly Thr Leu
225                 230                 235                 240

Leu Gln Lys Leu Arg Ala Lys Gly Ile Arg Asn Pro Asp His Ser Arg
                245                 250                 255

Ala Leu Ile Lys Glu Lys Leu Thr Ala Asp Pro Asp Ser Glu Val Ala
            260                 265                 270

Thr Thr Ser Leu Pro Gly Val Thr His Val Pro Ala Arg Lys Met Arg
        275                 280                 285

Leu Thr Val Pro Cys Arg Ala Leu Thr Cys Ala His Leu Gln Ser Phe
    290                 295                 300

Asp Ala Ala Leu Tyr Ile Gln Met Asn Glu Lys Lys Pro Thr Trp Thr
305                 310                 315                 320

Cys Pro Val Cys Asp Lys Lys Ala Pro Tyr Glu Ser Leu Ile Ile Asp
                325                 330                 335

Gly Leu Phe Met Glu Ile Leu Asn Ser Cys Ser Asp Cys Asp Glu Ile
```

-continued

```
                340                 345                 350
Gln Phe Met Glu Asp Gly Ser Trp Cys Pro Met Lys Pro Lys Lys Glu
            355                 360                 365
Ala Ser Glu Val Cys Pro Pro Gly Tyr Gly Leu Asp Gly Leu Gln
        370                 375                 380
Tyr Ser Ala Val Gln Glu Gly Ile Gln Pro Glu Ser Lys Lys Arg Val
385                 390                 395                 400
Glu Val Ile Asp Leu Thr Ile Glu Ser Ser Asp Glu Glu Asp Leu
                405                 410                 415
Pro Pro Thr Lys Lys Gln Cys Ser Val Thr Ser Ala Ala Ile Pro Ala
            420                 425                 430
Leu Leu Gly Ser Lys Gly Val Leu Thr Ser Gly His Gln Pro Ser Ser
            435                 440                 445
Val Leu Arg Ser Pro Ala Met Gly Thr Leu Gly Ser Asp Phe Leu Ser
        450                 455                 460
Ser Leu Pro Val His Glu Tyr Pro Pro Ala Phe Pro Leu Gly Ala Asp
465                 470                 475                 480
Ile Gln Gly Leu Asp Leu Phe Ser Phe Leu Gln Thr Glu Ser Gln Gln
                485                 490                 495
Tyr Gly Pro Ser Val Ile Ile Ser Leu Asp Glu Gln Asp Thr Leu Gly
            500                 505                 510
His Pro Phe Gln Tyr Arg Gly Thr Pro Ser His Phe Leu Gly Pro Leu
        515                 520                 525
Ala Pro Thr Leu Gly Ser Cys His Gly Ser Ser Thr Pro Ala Pro Pro
        530                 535                 540
Pro Gly Arg Val Ser Ser Ile Val Ala Pro Gly Ser Ser Leu Arg Glu
545                 550                 555                 560
Gly His Gly Gly Pro Leu Pro Ser Gly Pro Ser Leu Thr Gly Cys Arg
                565                 570                 575
Ser Asp Val Ile Ser Leu Asp
            580

<210> SEQ ID NO 8
<211> LENGTH: 572
<212> TYPE: PRT
<213> ORGANISM: Homo sapiens

<400> SEQUENCE: 8

Met Ala Asp Phe Glu Glu Leu Arg Asn Met Val Ser Ser Phe Arg Val
1               5                   10                  15
Ser Glu Leu Gln Val Leu Leu Gly Phe Ala Gly Arg Asn Lys Ser Gly
                20                  25                  30
Arg Lys His Asp Leu Leu Met Arg Ala Leu His Leu Leu Lys Ser Gly
            35                  40                  45
Cys Ser Pro Ala Val Gln Ile Lys Ile Arg Glu Leu Tyr Arg Arg Arg
        50                  55                  60
Tyr Pro Arg Thr Leu Glu Gly Leu Ser Asp Leu Ser Thr Ile Lys Ser
65                  70                  75                  80
Ser Val Phe Ser Leu Asp Gly Gly Ser Ser Pro Val Glu Pro Asp Leu
                85                  90                  95
Ala Val Ala Gly Ile His Ser Leu Pro Ser Thr Ser Val Thr Pro His
            100                 105                 110
Ser Pro Ser Ser Pro Val Gly Ser Val Leu Leu Gln Asp Thr Lys Pro
        115                 120                 125
Thr Phe Glu Met Gln Gln Pro Ser Pro Pro Ile Pro Pro Val His Pro
```

-continued

```
                130                 135                 140
Asp Val Gln Leu Lys Asn Leu Pro Phe Tyr Asp Val Leu Asp Val Leu
145                 150                 155                 160

Ile Lys Pro Thr Ser Leu Val Gln Ser Ser Ile Gln Arg Phe Gln Glu
                165                 170                 175

Lys Phe Phe Ile Phe Ala Leu Thr Pro Gln Gln Val Arg Glu Ile Cys
                180                 185                 190

Ile Ser Arg Asp Phe Leu Pro Gly Gly Arg Arg Asp Tyr Thr Val Gln
                195                 200                 205

Val Gln Leu Arg Leu Cys Leu Ala Glu Thr Ser Cys Pro Gln Glu Asp
            210                 215                 220

Asn Tyr Pro Asn Ser Leu Cys Ile Lys Val Asn Gly Lys Leu Phe Pro
225                 230                 235                 240

Leu Pro Gly Tyr Ala Pro Pro Lys Asn Gly Ile Glu Gln Lys Arg
                245                 250                 255

Pro Gly Arg Pro Leu Asn Ile Thr Ser Leu Val Arg Leu Ser Ser Ala
                260                 265                 270

Val Pro Asn Gln Ile Ser Ile Ser Trp Ala Ser Glu Ile Gly Lys Asn
                275                 280                 285

Tyr Ser Met Ser Val Tyr Leu Val Arg Gln Leu Thr Ser Ala Met Leu
                290                 295                 300

Leu Gln Arg Leu Lys Met Lys Gly Ile Arg Asn Pro Asp His Ser Arg
305                 310                 315                 320

Ala Leu Ile Lys Glu Lys Leu Thr Ala Asp Pro Asp Ser Glu Ile Ala
                325                 330                 335

Thr Thr Ser Leu Arg Val Ser Leu Met Cys Pro Leu Gly Lys Met Arg
                340                 345                 350

Leu Thr Ile Pro Cys Arg Ala Val Thr Cys Thr His Leu Gln Cys Phe
                355                 360                 365

Asp Ala Ala Leu Tyr Ile Gln Met Asn Glu Lys Lys Pro Thr Trp Ile
370                 375                 380

Cys Pro Val Cys Asp Lys Lys Ala Ala Tyr Glu Ser Leu Ile Leu Asp
385                 390                 395                 400

Gly Leu Phe Met Glu Ile Leu Asn Asp Cys Ser Asp Val Asp Glu Ile
                405                 410                 415

Lys Phe Gln Glu Asp Gly Ser Trp Cys Pro Met Arg Pro Lys Lys Glu
                420                 425                 430

Ala Met Lys Val Ser Ser Gln Pro Cys Thr Lys Ile Glu Ser Ser Ser
                435                 440                 445

Val Leu Ser Lys Pro Cys Ser Val Thr Val Ala Ser Glu Ala Ser Lys
450                 455                 460

Lys Lys Val Asp Val Ile Asp Leu Thr Ile Glu Ser Ser Ser Asp Glu
465                 470                 475                 480

Glu Glu Asp Pro Pro Ala Lys Arg Lys Cys Ile Phe Met Ser Glu Thr
                485                 490                 495

Gln Ser Ser Pro Thr Lys Gly Val Leu Met Tyr Gln Pro Ser Ser Val
                500                 505                 510

Arg Val Pro Ser Val Thr Ser Val Asp Pro Ala Ala Ile Pro Pro Ser
                515                 520                 525

Leu Thr Asp Tyr Ser Val Pro Phe His His Thr Pro Ile Ser Ser Met
                530                 535                 540

Ser Ser Asp Leu Pro Gly Glu Gln Arg Phe Asn Asp Ile Asn Asn Glu
545                 550                 555                 560
```

```
Leu Lys Leu Gly Thr Ser Ser Asp Thr Val Gln Gln
            565                 570
```

<210> SEQ ID NO 9
<211> LENGTH: 621
<212> TYPE: PRT
<213> ORGANISM: Homo sapiens

<400> SEQUENCE: 9

```
Met Ala Asp Phe Glu Glu Leu Arg Asn Met Val Ser Ser Phe Arg Val
 1               5                  10                  15

Ser Glu Leu Gln Val Leu Leu Gly Phe Ala Gly Arg Asn Lys Ser Gly
                20                  25                  30

Arg Lys His Asp Leu Leu Met Arg Ala Leu His Leu Leu Lys Ser Gly
            35                  40                  45

Cys Ser Pro Ala Val Gln Ile Lys Ile Arg Glu Leu Tyr Arg Arg Arg
        50                  55                  60

Tyr Pro Arg Thr Leu Glu Gly Leu Ser Asp Leu Ser Thr Ile Lys Ser
 65                  70                  75                  80

Ser Val Phe Ser Leu Asp Gly Gly Ser Ser Pro Val Glu Pro Asp Leu
                85                  90                  95

Ala Val Ala Gly Ile His Ser Leu Pro Ser Thr Ser Val Thr Pro His
            100                 105                 110

Ser Pro Ser Ser Pro Val Gly Ser Val Leu Leu Gln Asp Thr Lys Pro
        115                 120                 125

Thr Phe Glu Met Gln Gln Pro Ser Pro Ile Pro Pro Val His Pro
    130                 135                 140

Asp Val Gln Leu Lys Asn Leu Pro Phe Tyr Asp Val Leu Asp Val Leu
145                 150                 155                 160

Ile Lys Pro Thr Ser Leu Val Gln Ser Ser Ile Gln Arg Phe Gln Glu
                165                 170                 175

Lys Phe Phe Ile Phe Ala Leu Thr Pro Gln Gln Val Arg Glu Ile Cys
            180                 185                 190

Ile Ser Arg Asp Phe Leu Pro Gly Gly Arg Arg Asp Tyr Thr Val Gln
        195                 200                 205

Val Gln Leu Arg Leu Cys Leu Ala Glu Thr Ser Cys Pro Gln Glu Asp
    210                 215                 220

Asn Tyr Pro Asn Ser Leu Cys Ile Lys Val Asn Gly Lys Leu Phe Pro
225                 230                 235                 240

Leu Pro Gly Tyr Ala Pro Pro Lys Asn Gly Ile Glu Gln Lys Arg
                245                 250                 255

Pro Gly Arg Pro Leu Asn Ile Thr Ser Leu Val Arg Leu Ser Ser Ala
            260                 265                 270

Val Pro Asn Gln Ile Ser Ile Ser Trp Ala Ser Glu Ile Gly Lys Asn
        275                 280                 285

Tyr Ser Met Ser Val Tyr Leu Val Arg Gln Leu Thr Ser Ala Met Leu
    290                 295                 300

Leu Gln Arg Leu Lys Met Lys Gly Ile Arg Asn Pro Asp His Ser Arg
305                 310                 315                 320

Ala Leu Ile Lys Glu Lys Leu Thr Ala Asp Pro Asp Ser Glu Ile Ala
                325                 330                 335

Thr Thr Ser Leu Arg Val Ser Leu Met Cys Pro Leu Gly Lys Met Arg
            340                 345                 350

Leu Thr Ile Pro Cys Arg Ala Val Thr Cys Thr His Leu Gln Cys Phe
        355                 360                 365
```

```
Asp Ala Ala Leu Tyr Ile Gln Met Asn Glu Lys Lys Pro Thr Trp Ile
        370                 375                 380

Cys Pro Val Cys Asp Lys Lys Ala Ala Tyr Glu Ser Leu Ile Leu Asp
385                 390                 395                 400

Gly Leu Phe Met Glu Ile Leu Asn Asp Cys Ser Asp Val Asp Glu Ile
                    405                 410                 415

Lys Phe Gln Glu Asp Gly Ser Trp Cys Pro Met Arg Pro Lys Lys Glu
                420                 425                 430

Ala Met Lys Val Ser Ser Gln Pro Cys Thr Lys Ile Glu Ser Ser Ser
            435                 440                 445

Val Leu Ser Lys Pro Cys Ser Val Thr Val Ala Ser Glu Ala Ser Lys
        450                 455                 460

Lys Lys Val Asp Val Ile Asp Leu Thr Ile Glu Ser Ser Ser Asp Glu
465                 470                 475                 480

Glu Glu Asp Pro Pro Ala Lys Arg Lys Cys Ile Phe Met Ser Glu Thr
                485                 490                 495

Gln Ser Ser Pro Thr Lys Gly Val Leu Met Tyr Gln Pro Ser Ser Val
                500                 505                 510

Arg Val Pro Ser Val Thr Ser Val Asp Pro Ala Ile Pro Pro Ser
            515                 520                 525

Leu Thr Asp Tyr Ser Val Pro Phe His His Thr Pro Ile Ser Ser Met
        530                 535                 540

Ser Ser Asp Leu Pro Gly Leu Asp Phe Leu Ser Leu Ile Pro Val Asp
545                 550                 555                 560

Pro Gln Tyr Cys Pro Pro Met Phe Leu Asp Ser Leu Thr Ser Pro Leu
                565                 570                 575

Thr Ala Ser Ser Thr Ser Val Thr Thr Thr Ser Ser His Glu Ser Ser
            580                 585                 590

Thr His Val Ser Ser Ser Ser Arg Ser Glu Thr Gly Val Ile Thr
        595                 600                 605

Ser Ser Gly Ser Asn Ile Pro Glu Ile Ile Ser Leu Asp
        610                 615                 620

<210> SEQ ID NO 10
<211> LENGTH: 510
<212> TYPE: PRT
<213> ORGANISM: Homo sapiens

<400> SEQUENCE: 10

Met Ala Ala Glu Leu Val Glu Ala Lys Asn Met Val Met Ser Phe Arg
1               5                   10                  15

Val Ser Asp Leu Gln Met Leu Leu Gly Phe Val Gly Arg Ser Lys Ser
                20                  25                  30

Gly Leu Lys His Glu Leu Val Thr Arg Ala Leu Gln Leu Val Gln Pro
            35                  40                  45

Asp Cys Ser Pro Glu Leu Phe Lys Lys Ile Lys Glu Leu Tyr Glu Thr
        50                  55                  60

Arg Tyr Ala Lys Lys Asn Ser Glu Pro Ala Pro Gln Pro His Arg Pro
65                  70                  75                  80

Leu Asp Pro Leu Thr Met His Ser Thr Tyr Asp Arg Ala Gly Ala Val
                85                  90                  95

Pro Arg Thr Pro Leu Ala Gly Phe Asn Ile Asp Tyr Pro Val Leu Tyr
                100                 105                 110

Gly Lys Tyr Leu Asn Gly Leu Gly Arg Leu Pro Ala Lys Thr Leu Lys
            115                 120                 125
```

```
Pro Glu Val Arg Leu Val Lys Leu Pro Phe Phe Asn Met Leu Asp Glu
130                 135                 140

Leu Leu Lys Pro Thr Glu Leu Val Pro Gln Asn Asn Glu Lys Leu Gln
145                 150                 155                 160

Glu Ser Pro Cys Ile Phe Ala Leu Thr Pro Arg Gln Val Glu Leu Ile
                165                 170                 175

Arg Phe Lys Gln Gly Met Gln Pro Gly Val Lys Ala Val Gln Val Val
                180                 185                 190

Leu Arg Ile Cys Tyr Ser Asp Thr Ser Cys Pro Gln Glu Asp Gln Tyr
            195                 200                 205

Pro Pro Asn Ile Ala Val Lys Val Asn His Ser Tyr Cys Ser Val Pro
210                 215                 220

Gly Tyr Tyr Pro Ser Asn Lys Pro Gly Val Glu Pro Lys Arg Pro Cys
225                 230                 235                 240

Arg Pro Ile Asn Leu Thr His Leu Met Tyr Leu Ser Ser Ala Thr Asn
                245                 250                 255

Arg Ile Thr Val Thr Trp Gly Asn Tyr Gly Lys Ser Tyr Ser Val Ala
                260                 265                 270

Leu Tyr Leu Val Arg Gln Leu Thr Ser Ser Glu Leu Leu Gln Arg Leu
            275                 280                 285

Lys Thr Ile Gly Val Lys His Pro Glu Leu Cys Lys Ala Leu Val Lys
290                 295                 300

Glu Lys Leu Arg Leu Asp Pro Asp Ser Glu Ile Ala Thr Thr Gly Val
305                 310                 315                 320

Arg Val Ser Leu Ile Cys Pro Leu Val Lys Met Arg Leu Ser Val Pro
                325                 330                 335

Cys Arg Ala Glu Thr Cys Ala His Leu Gln Cys Phe Asp Ala Val Phe
                340                 345                 350

Tyr Ile Gln Met Asn Glu Lys Lys Pro Thr Trp Met Cys Pro Val Cys
            355                 360                 365

Asp Lys Pro Ala Pro Tyr Asp Gln Leu Ile Ile Asp Gly Leu Leu Ser
370                 375                 380

Lys Ile Leu Ser Glu Cys Glu Asp Ala Asp Glu Ile Glu Tyr Leu Val
385                 390                 395                 400

Asp Gly Ser Trp Cys Pro Ile Arg Ala Glu Lys Glu Arg Ser Cys Ser
                405                 410                 415

Pro Gln Gly Ala Ile Leu Val Leu Gly Pro Ser Asp Ala Asn Gly Leu
                420                 425                 430

Leu Pro Ala Pro Ser Val Asn Gly Ser Gly Ala Leu Gly Ser Thr Gly
            435                 440                 445

Gly Gly Gly Pro Val Gly Ser Met Glu Asn Gly Lys Pro Gly Ala Asp
450                 455                 460

Val Val Asp Leu Thr Leu Asp Ser Ser Ser Ser Glu Asp Glu
465                 470                 475                 480

Glu Glu Glu Glu Glu Glu Asp Glu Asp Glu Glu Gly Pro Arg Pro
                485                 490                 495

Lys Arg Arg Cys Pro Phe Gln Lys Gly Leu Val Pro Ala Cys
                500                 505                 510
```